(12) United States Patent
Kinoshita

(10) Patent No.: US 11,779,290 B2
(45) Date of Patent: Oct. 10, 2023

(54) X-RAY IMAGING SYSTEM AND X-RAY IMAGING APPARATUS

(71) Applicant: SHIMADZU CORPORATION, Kyoto (JP)

(72) Inventor: Hiroyuki Kinoshita, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 223 days.

(21) Appl. No.: 17/497,416

(22) Filed: Oct. 8, 2021

(65) Prior Publication Data

US 2022/0110593 A1    Apr. 14, 2022

Related U.S. Application Data

(60) Provisional application No. 63/089,641, filed on Oct. 9, 2020.

(30) Foreign Application Priority Data

Aug. 30, 2021    (JP) ................. 2021-140336

(51) Int. Cl.
  *A61B 6/04*    (2006.01)
  *A61B 6/00*    (2006.01)
  *G06T 7/70*    (2017.01)

(52) U.S. Cl.
  CPC ............ *A61B 6/0492* (2013.01); *A61B 6/463* (2013.01); *G06T 7/70* (2017.01); *G06T 2207/10116* (2013.01); *G06T 2207/30196* (2013.01)

(58) Field of Classification Search
  None
  See application file for complete search history.

(56) References Cited

U.S. PATENT DOCUMENTS

| | | |
|---|---|---|
| 2011/0249792 A1 | 10/2011 | Lalena et al. |
| 2011/0249793 A1 | 10/2011 | Lalena et al. |
| 2011/0249799 A1 | 10/2011 | Lalena et al. |
| 2012/0039447 A1 | 2/2012 | Lalena et al. |

(Continued)

FOREIGN PATENT DOCUMENTS

JP    2013-523396 A    6/2013

OTHER PUBLICATIONS

"Philips-DigitalDiagnost C90 Ceiling-traveling digital X-ray equipment", Phillips, 4 pages, https://www.philips.co.jp/healthcare/product/HC712034/digitaldiagnost-c90-x, Oct. 9, 2020.

(Continued)

*Primary Examiner* — Hoon K Song
(74) *Attorney, Agent, or Firm* — Sughrue Mion, PLLC

(57) ABSTRACT

An X-ray imaging system includes an X-ray irradiation unit, an X-ray detection unit, an imaging unit that acquires a subject image obtained by imaging an appearance of the subject, a position information acquisition unit that acquires a position information of the subject captured in the subject image, a target position acquisition unit that acquires a target position according to imaging conditions, and a projection unit that projects a marker indicating a contour of the subject for guiding a position of the subject to be the target position acquired by the target position acquisition unit, onto an imaging position that is the subject or a surface to which the subject is fixed.

16 Claims, 12 Drawing Sheets

(56) References Cited

U.S. PATENT DOCUMENTS

| | | | | |
|---|---|---|---|---|
| 2016/0073979 | A1* | 3/2016 | Braun | A61B 6/0492 5/601 |
| 2017/0224298 | A1* | 8/2017 | Hannemann | A61B 6/469 |
| 2018/0070902 | A1* | 3/2018 | Lin | A61B 5/1079 |
| 2020/0013147 | A1* | 1/2020 | Miyajima | G06T 7/70 |
| 2020/0138394 | A1* | 5/2020 | Vanden Berghe | G16H 50/30 |
| 2021/0393218 | A1* | 12/2021 | Jaber | A61B 6/08 |

OTHER PUBLICATIONS

"Digital Radiography AccE GM85", Samsung Healthcare Global—Accelerating Experience AccE GM85, 8 pages, https://www.samsunghealthcare.com/en/products/DigitalRadiography//AccE%20GM85/Radiology/benefit, Oct. 9, 2020.

"The world's first surgical guide system that applies projection mapping technology "—Medical Imaging Projection System—MIPS"—Industry-govemment-academia collaborative development project finally put into practical use—", Japan Agency for Medical Research and Development, 4 pages, https://www.amed.go.jp/news/release_20200203html, Oct. 9, 2020.

* cited by examiner

SUBJECT IMAGE

SUBJECT TARGET IMAGE

FIG. 13
STATE IN WHICH POSITION AND POSTURE OF SUBJECT
HAVE NOT BECOME TARGET POSITION AND TARGET POSTURE
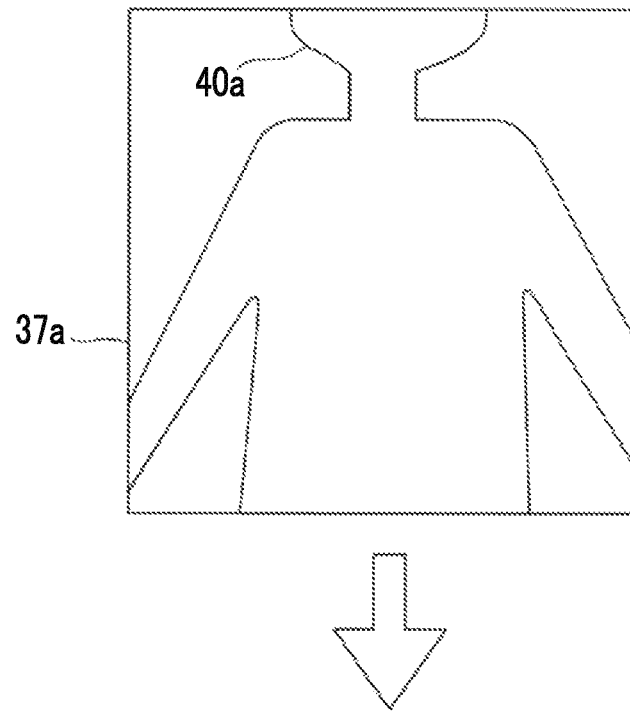
STATE IN WHICH POSITION AND POSTURE OF SUBJECT
HAVE BECOME TARGET POSITION AND TARGET POSTURE
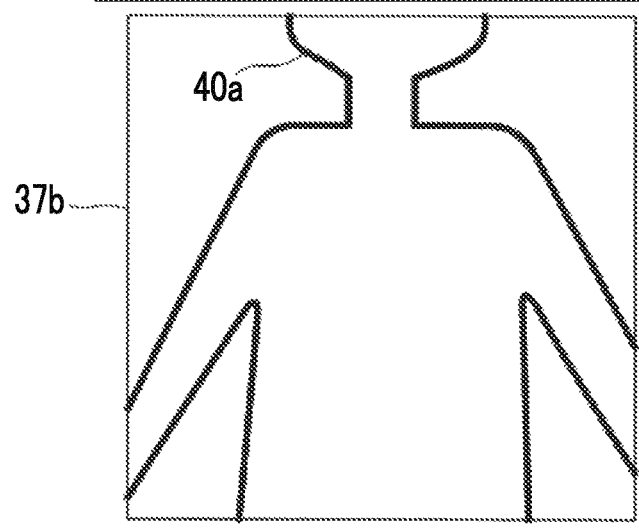

NOTIFICATION PROCESS

MODIFICATION EXAMPLE

X-RAY IMAGING SYSTEM AND X-RAY IMAGING APPARATUS

CROSS-REFERENCE TO RELATED APPLICATIONS

The priority application number U.S. Ser. No. 63/089,641, PREPARATION SUPPORT DEVICE FOR X-RAY PHOTOGRAPHY, Oct. 9, 2020, KINOSHITA Hiroyuki, the priority application number JP2021-140336, X-RAY IMAGING SYSTEM AND X-RAY IMAGING APPARATUS, Aug. 30, 2021, KINOSHITA Hiroyuki, upon which this patent application are based hereby incorporated by reference.

BACKGROUND OF THE INVENTION

Field of the Invention

The present invention relates to an X-ray imaging system and an X-ray imaging apparatus, and more particularly to an X-ray imaging system and an X-ray imaging apparatus that assist in adjusting relative positions between an X-ray irradiation unit, an X-ray detection unit, and a subject.

Background Art

In the related art, there are known X-ray imaging systems and X-ray imaging apparatuses that assist in adjusting relative positions between an X-ray irradiation unit, an X-ray detection unit, and a subject. Such X-ray imaging systems and X-ray imaging apparatuses are disclosed in, for example, PCT Japanese Translation Patent Publication No. 2013-523396.

A radiographic imaging apparatus (X-ray imaging system) disclosed in PCT Japanese Translation Patent Publication No. 2013-523396 includes a radiation source, a receiver, a collimator, and a display device. The collimator disclosed in PCT Japanese Translation Patent Publication No. 2013-523396 is provided with a sensor element. PCT Japanese Translation Patent Publication No. 2013-523396 discloses a configuration including a holder that holds the receiver. The holder holds an electromagnetic coil together with the receiver. PCT Japanese Translation Patent Publication No. 2013-523396 discloses a configuration in which a relative position between the radiation source and the receiver is detected by detecting an electromagnetic wave emitted from the electromagnetic coil held in the holder by the sensor element provided in the collimator.

PCT Japanese Translation Patent Publication No. 2013-523396 discloses a configuration in which information referred to by an operator when adjusting relative positions between the radiation source, the receiver, and a subject is displayed on the display device. Specifically, PCT Japanese Translation Patent Publication No. 2013-523396 discloses a configuration in which a distance between the radiation source and the receiver, an angle of the radiation source with respect to the subject, a position of an optical axis of radiation emitted from the radiation source, and the like are displayed on the display device as the information referred to by the operator when adjusting the relative positions between the radiation source, the receiver, and the subject. That is, in the configuration disclosed in PCT Japanese Translation Patent Publication No. 2013-523396, the operator adjusts the relative positions between the radiation source, the receiver, and the subject while viewing the display device.

However, as disclosed in PCT Japanese Translation Patent Publication No. 2013-523396, in the configuration in which the relative positions between the radiation source (X-ray irradiation unit), the receiver (X-ray detection unit), and the subject are adjusted while checking the information displayed on the display device, the operator adjusts the relative positions between the X-ray irradiation unit, the X-ray detection unit, and the subject while alternately moving the line of sight between the display device and the subject. Therefore, there is a problem in that the efficiency of adjusting the relative positions between the X-ray irradiation unit, the X-ray detection unit, and the subject decreases as the operator's line of sight moves alternately.

SUMMARY OF THE INVENTION

The present invention has been made to solve the above-described problems, and one object of the present invention is to provide an X-ray imaging system and an X-ray imaging apparatus capable of suppressing a decrease in efficiency of adjusting relative positions between an X-ray irradiation unit, an X-ray detection unit, and a subject by suppressing an operator from moving the line of sight.

In order to achieve the object, according to a first aspect of the present invention, there is provided an X-ray imaging system including an X-ray irradiation unit that irradiates a subject with X-rays; an X-ray detection unit that detects the X-rays radiated from the X-ray irradiation unit; an imaging unit that acquires a subject image obtained by imaging an appearance of the subject; a position information acquisition unit that acquires a position information of the subject captured in the subject image on the basis of the subject image; a target position acquisition unit that acquires a target position according to imaging conditions on the basis of the imaging conditions and the position information; and a projection unit that projects a marker indicating a contour of the subject for guiding a position of the subject to be the target position acquired by the target position acquisition unit, onto an imaging position that is the subject or a surface to which the subject is fixed.

In order to achieve the object, according to a second aspect of the present invention, there is provided an X-ray imaging apparatus including an X-ray irradiation unit that irradiates a subject with X-rays; an X-ray detection unit that detects the X-rays radiated from the X-ray irradiation unit; an imaging unit that acquires a subject image obtained by imaging an appearance of the subject; a position information acquisition unit that acquires a position information of the subject captured in the subject image on the basis of the subject image; a target position acquisition unit that acquires a target position according to imaging conditions on the basis of the imaging conditions and the position information; and a projection unit that projects a marker indicating a contour of the subject for guiding a position of the subject to be the target position acquired by the target position acquisition unit, onto an imaging position that is the subject or a surface to which the subject is fixed.

As described above, the X-ray imaging system of the first aspect includes the target position acquisition unit that acquires a target position according to imaging conditions on the basis of the imaging conditions and the position information of the subject and the projection unit that projects a marker indicating a contour of the subject for guiding a position of the subject to be the target position acquired by the target position acquisition unit, onto an imaging position that is the subject or a surface to which the subject is fixed. Consequently, the marker indicating the contour of the subject for guiding the subject to the target position according to the imaging conditions is projected onto the imaging position, and thus an operator can adjust relative positions between the X-ray irradiation unit, the X-ray detection unit, and the subject while checking the marker projected on the imaging position. That is, the operator can adjust the relative positions between the X-ray irradiation unit, the X-ray detection unit, and the subject without moving the line of sight from the subject. As a result, it is possible to provide the X-ray imaging apparatus capable of suppressing a decrease in the efficiency of adjusting the relative positions between the X-ray irradiation unit, the X-ray detection unit, and the subject by suppressing the operator from moving the line of sight.

Since the projection unit projecting the marker is provided, the marker for guiding the position of the subject is projected, and thus relative positions between the X-ray irradiation unit, the X-ray detection unit, and the subject can be adjusted to appropriate positions regardless of a skill level of the operator. Since the projection unit projecting the marker is provided, the operator can check whether relative positions between the X-ray irradiation unit, the X-ray detection unit, and the subject are appropriate before performing X-ray imaging. As a result, it is possible to suppress re-imaging due to inappropriate relative positions between the X-ray irradiation unit, the X-ray detection unit, and the subject, and thus to suppress an increase an exposure dose of the subject due to the re-imaging.

As described above, the X-ray imaging apparatus of the second aspect includes the target position acquisition unit that acquires a target position according to imaging conditions on the basis of the imaging conditions and the position information of the subject and the projection unit that projects a marker indicating a contour of the subject for guiding a position of the subject to be the target position acquired by the target position acquisition unit, onto an imaging position that is the subject or a surface to which the subject is fixed. Consequently, in the same manner as in the X-ray imaging system of the first aspect, it is possible to provide the X-ray imaging apparatus capable of suppressing a decrease in the efficiency of adjusting the relative positions between the X-ray irradiation unit, the X-ray detection unit, and the subject by suppressing the operator from moving the line of sight.

BRIEF DESCRIPTION OF THE DRAWINGS

FIG. 13 is a schematic diagram for describing a configuration in which a notification unit according to the embodiment notifies that a position and a posture of the subject become the target position and the target posture.

DETAILED DESCRIPTION OF THE INVENTION

Configuration of X-Ray Imaging Apparatus

A configuration of an X-ray imaging system 100 according to an embodiment will be described with reference to FIG. 1.

Figure 1:
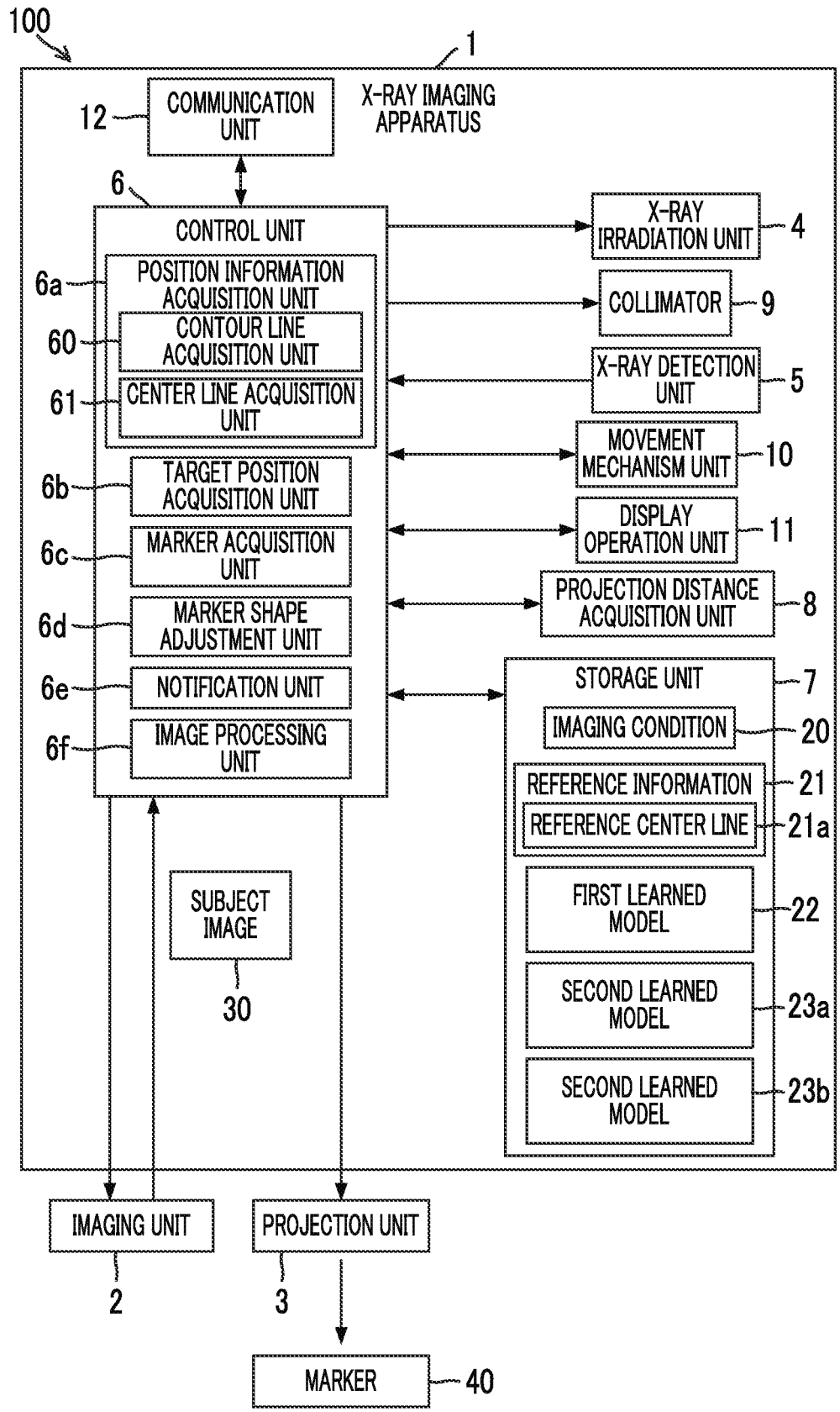
FIG. 1 is a block diagram illustrating the overall configuration of an X-ray imaging system according to an embodiment.

As illustrated in FIG. 1, the X-ray imaging system 100 includes an X-ray imaging apparatus 1, an imaging unit 2, and a projection unit 3. The imaging unit 2 and the projection unit 3 are provided in the X-ray imaging apparatus 1.

The imaging unit 2 is configured to acquire a subject image 30 in which an appearance of a subject 90 (refer to FIG. 3) is imaged. In the present embodiment, the imaging unit 2 is configured to acquire an image of the subject 90 with light other than X-rays. For example, the imaging unit 2 includes any of a visible light camera acquires an image of the subject 90 with visible light, an infrared camera that acquires an image of the subject 90 with infrared rays, and an ultraviolet camera that acquires an image of the subject 90 with ultraviolet rays. In the present embodiment, the imaging unit 2 is a visible light camera. That is, the imaging unit 2 includes, for example, a charge coupled device (CCD) sensor or a complementary metal oxide semiconductor (CMOS) sensor.

Figure 3:
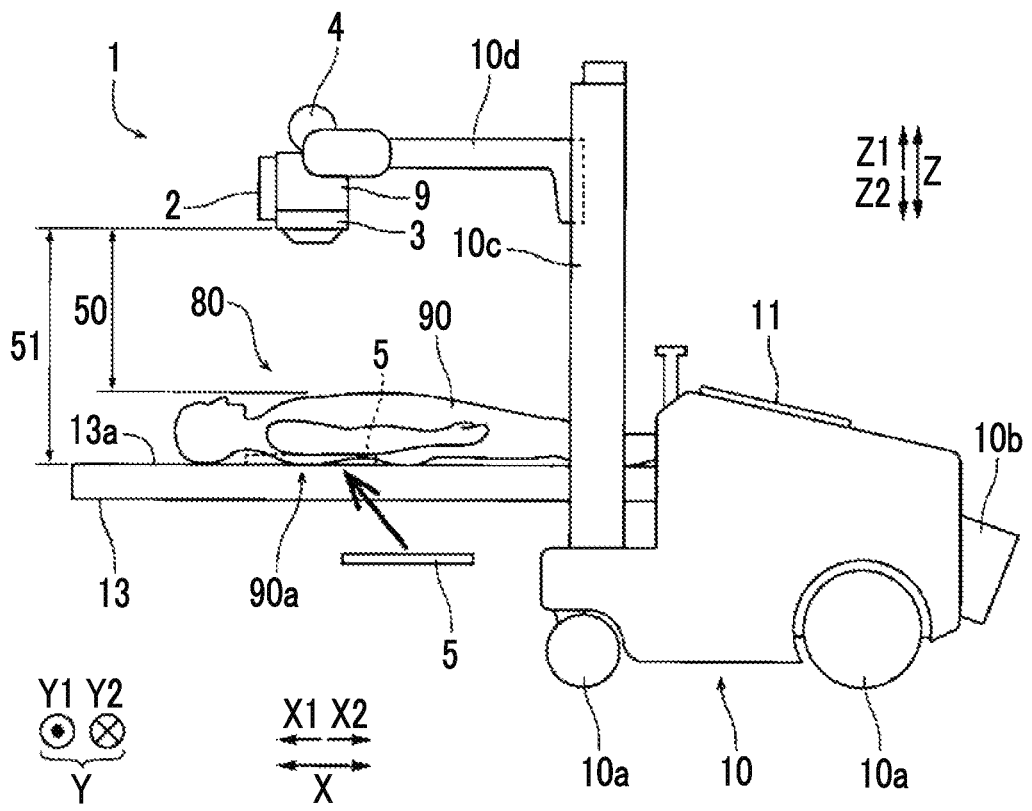
FIG. 3 is a side view illustrating a state at the time of imaging in the X-ray imaging apparatus according to the embodiment.

The projection unit 3 is configured to project a marker 40 onto an imaging position 80 (refer to FIG. 3). The imaging position 80 is the subject 90 or a surface 13a (refer to FIG. 3) to which the subject 90 is fixed. The imaging position 80 is a position where the subject 90 is disposed when the X-ray imaging apparatus 1 images the subject 90. The projection unit 3 includes, for example, a projector.

The X-ray imaging apparatus 1 according to the present embodiment includes an X-ray irradiation unit 4, an X-ray detection unit 5, and a control unit 6. In the present embodiment, the X-ray imaging apparatus 1 includes a storage unit 7. In the present embodiment, the X-ray imaging apparatus 1 includes a projection distance acquisition unit 8. In the present embodiment, the X-ray imaging apparatus 1 includes a collimator 9, a movement mechanism unit 10, a display operation unit 11, and a communication unit 12.

The X-ray irradiation unit 4 is configured to irradiate the subject 90 (refer to FIG. 3) with X-rays. The X-ray irradiation unit 4 is configured to radiate X-rays by a voltage being radiated by an X-ray tube driving unit (not illustrated). The X-ray irradiation unit 4 includes, for example, an X-ray irradiation device provided with an X-ray tube.

The X-ray detection unit 5 is configured to detect the X-rays radiated from the X-ray irradiation unit 4. The X-ray detection unit 5 includes a light receiving unit that receives X-rays radiated from the X-ray irradiation unit 4 and a conversion unit that converts the X-rays received by the light receiving unit into an image signal. The X-ray detection unit 5 is configured with, for example, a plurality of conversion elements (not illustrated) and pixel electrodes (not illustrated) disposed on the plurality of conversion elements. The X-ray detection unit 5 includes, for example, a flat panel detector (FPD). In the present embodiment, the X-ray detection unit 5 is configured as a wireless type X-ray detector, and can be separated from the X-ray imaging apparatus 1 and carried. The X-ray detection unit 5 is configured to be housed in a housing 10b (refer to FIG. 2) that will be described later, except during X-ray imaging.

The control unit 6 is configured such that an image obtained through X-ray imaging can be displayed on the display operation unit 11. The control unit 6 is configured to control various constituents of the X-ray imaging apparatus 1 on the basis of an operation input by the display operation unit 11. The control unit 6 is a processor configured to include, for example, a central processing unit (CPU), a graphics processing unit (GPU), a field-programmable gate array (FPGA) configured for image processing, a read only memory (ROM), and a random access memory (RAM).

The control unit 6 includes a position information acquisition unit 6a and a target position acquisition unit 6b as functional blocks of software (program). The control unit 6 includes a marker acquisition unit 6c as a functional block of software. The control unit 6 includes a marker shape adjustment unit 6d as a functional block of the software. The control unit 6 includes a notification unit 6e as a functional block of software. The control unit 6 includes an image processing unit 6f as a functional block of software. The position information acquisition unit 6a, the target position acquisition unit 6b, the marker acquisition unit 6c, the marker shape adjustment unit 6d, the notification unit 6e, and the image processing unit 6f may be provided with dedicated processors (processing circuits) to be individually configured by hardware.

Figure 4:
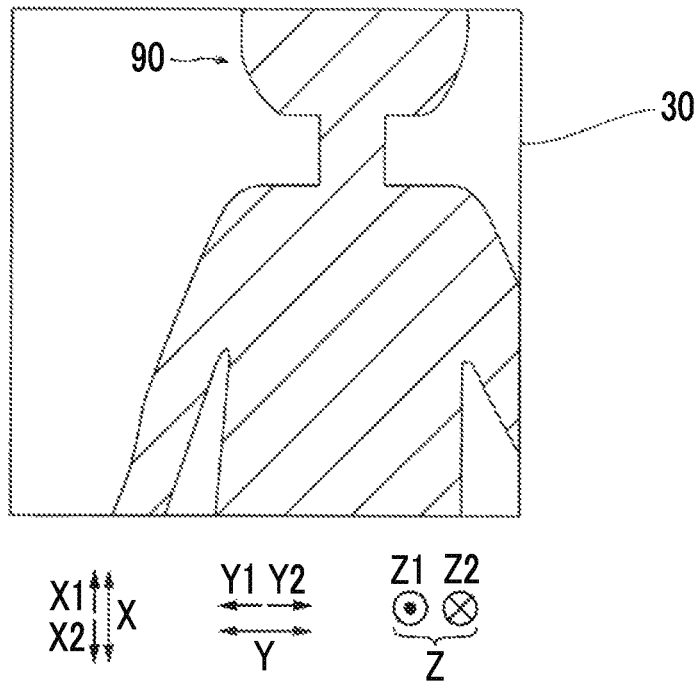
FIG. 4 is a schematic diagram for describing a subject image captured by an imaging unit according to the embodiment.

The position information acquisition unit 6a is configured to acquire position information of the subject (refer to FIG. 3) captured in the subject image 30 on the basis of the subject image 30 (refer to FIG. 4). In the present embodiment, the position information acquisition unit 6a includes a contour line acquisition unit 60 that acquires a contour line 90b (refer to FIG. 6) of the subject 90 on the basis of the subject image 30, and a center line acquisition unit 61 that acquires a center line 90c (refer to FIG. 6) of the subject 90 captured in the subject image 30. Details of a configuration in which the position information acquisition unit 6a acquires the contour line 90b and the center line 90c will be described later.

The target position acquisition unit 6b is configured to acquire a target position according to imaging conditions 20 on the basis of the imaging conditions 20 and the position information. Details of a configuration in which the target position acquisition unit 6b acquires the target position will be described later. The imaging conditions 20 are conditions at the time of imaging, including an imaging part of the subject 90 and an imaging direction. The imaging conditions 20 include, for example, the chest as the imaging part. The imaging conditions 20 include, for example, the front as the imaging direction.

The marker acquisition unit 6c is configured to acquire the marker 40. Details of a configuration in which the marker acquisition unit 6c acquires the marker 40 and details of the marker 40 acquired by the marker acquisition unit 6c will be described later.

The marker shape adjustment unit 6d is configured to adjust a shape of the marker 40 on the basis of a projection distance acquired by the projection distance acquisition unit 8. Details of a configuration in which the marker shape adjustment unit 6d adjusts a shape of the marker 40 will be described later.

The notification unit 6e is configured to perform a notification when a position and a posture of the subject 90 (refer to FIG. 3) become a target position and a target posture. Details of a configuration in which the notification unit 6e performs a notification will be described later.

The image processing unit 6f is configured to generate an X-ray image (not illustrated) on the basis of an intensity distribution of X-rays detected by the X-ray detection unit 5.

The storage unit 7 includes, for example, a non-volatile storage device. Various programs used for processes in the control unit 6 are stored in the storage unit 7. The storage unit 7 is configured to store reference information 21 that is information regarding a reference position and a reference posture according to the imaging conditions 20. The reference information 21 includes a reference center line 21a (refer to FIG. 7) that is a center line 90c (refer to FIG. 6) of the subject 90 when the subject 90 takes a reference position and a reference posture. In the present embodiment, the reference information 21 is stored in the storage unit 7 in a state of being associated with the imaging conditions 20. That is, the reference center line 21a appropriate for the imaging part and the imaging direction included in the imaging conditions 20 is stored in the storage unit 7 for each of the imaging conditions 20. The storage unit 7 stores a first learned model 22, a second learned model 23a, and the second learned model 23b. Details of the first learned model 22, the second learned model 23a, and the second learned model 23b will be described later.

The projection distance acquisition unit 8 is configured to acquire a projection distance that is a distance 50 (refer to FIG. 3) between the projection unit 3 and the subject 90 or a distance 51 (refer to FIG. 3) between the projection unit 3 and the surface 13a (refer to FIG. 3) to which the subject 90 is fixed. In the present embodiment, the projection distance acquisition unit 8 includes a light source that radiates infrared rays, a scanner that performs scanning with the infrared rays radiated from the light source, and a detector that detects the infrared rays radiated from the light source and captured by a detection target (for example, the subject 90). That is, the projection distance acquisition unit 8 includes an infrared scanner that acquires a distance to each point of a detection target with infrared rays. Details of a configuration in which the projection distance acquisition unit 8 acquires a projection distance will be described later.

The collimator 9 is configured such that an irradiation range of X-rays radiated from the X-ray irradiation unit 4 can be adjusted.

The movement mechanism unit 10 is configured to be movable in a state of supporting the X-ray irradiation unit 4. A detailed configuration of the movement mechanism unit 10 will be described later.

The display operation unit 11 is configured as, for example, a touch panel type liquid crystal display. The display operation unit 11 is configured to function as a display unit on which X-ray imaging is displayed and an input unit to which various operations are input.

The communication unit 12 is configured to be able to communicate with an external network, and is configured to be able to acquire the imaging conditions 20 for the subject 90 from the outside or transmit an image obtained through the X-ray imaging to the outside.

Apparatus Configuration

Figure 2:
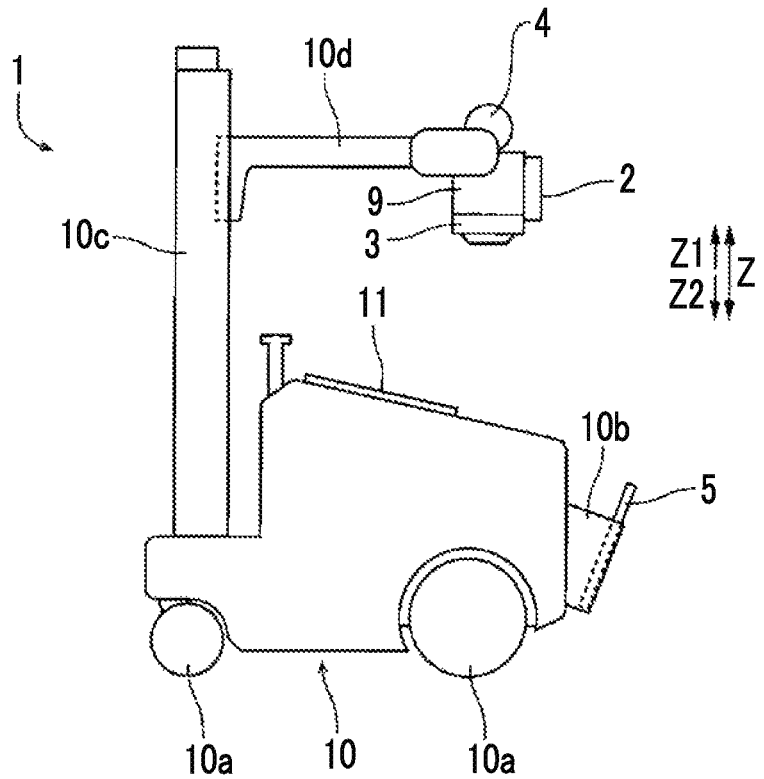
FIG. 2 is a side view illustrating the overall configuration of an X-ray imaging apparatus included in the X-ray imaging system according to the embodiment.

As illustrated in FIG. 2, the X-ray imaging apparatus 1 according to the present embodiment is movable as a whole, and is configured to be able to be moved to a patient (the subject 90; refer to FIG. 3) in each hospital room at the time of rounds and to perform X-ray imaging. That is, the X-ray imaging apparatus 1 according to the present embodiment is a so-called rounds imaging apparatus.

In the X-ray imaging apparatus 1, the X-ray irradiation unit 4, the X-ray detection unit 5, and the display operation unit 11 are provided in the movement mechanism unit 10. The projection unit 3 is provided in the vicinity of the X-ray irradiation unit 4. The imaging unit 2 and the collimator 9 are provided in the vicinity of the X-ray irradiation unit 4. Specifically, a collimator 9 is provided for the X-ray irradiation unit 4. The imaging unit 2 and the projection unit 3 are provided at the collimator 9. That is, the imaging unit 2, the projection unit 3, the X-ray irradiation unit 4, and the collimator 9 are provided in the X-ray imaging apparatus 1 as one unit. In the present embodiment, an up-down direction is set to a Z direction. In the Z direction, the up direction is set to a Z1 direction and the down direction is set to a Z2 direction. The vicinity of the X-ray irradiation unit 4 refers to including both a position of the X-ray irradiation unit 4 and the vicinity of the position of the X-ray irradiation unit 4.

The movement mechanism unit 10 is configured as a trolley of the X-ray imaging apparatus 1. A power supply device, a battery, and the like for supplying electric power for moving and imaging the X-ray imaging apparatus 1 are provided inside the movement mechanism unit 10. The movement mechanism unit 10 is provided with a plurality of wheels 10a, a housing 10b, a support column 10c, and an arm 10d.

The plurality of wheels 10a are provided at the lower part of the movement mechanism unit 10. Consequently, it is possible to move the X-ray imaging apparatus 1.

The housing 10b is provided at the rear part of the movement mechanism unit 10. The housing 10b is configured such that the X-ray detection unit 5 can be taken out and housed.

The movement mechanism unit 10 is provided with the support column 10c. Specifically, the support column 10c is attached to the front part of the movement mechanism unit 10 so as to extend in the vertical direction (Z direction). The support column 10c holds the arm 10d to be movable up and down. The X-ray irradiation unit 4, the imaging unit 2, the projection unit 3, and the collimator are provided at the arm 10d. That is, the X-ray irradiation unit 4, the imaging unit 2, the projection unit 3, and the collimator 9 are configured to be movable up and down as the arm 10d moves up and down. The support column 10c is configured to be rotatable in a rotation direction about the vertical axis.

The arm 10d is attached to extend in the horizontal direction from the support column 10c. The arm 10d is configured to be movable up and down with respect to the support column 10c. The arm 10d is configured to be expandable and contractible such that a horizontal position of the X-ray irradiation unit 4 can be changed.

As illustrated in FIG. 3, when imaging the subject 90, an operator disposes the X-ray irradiation unit 4 in front of the support column 10c (X1 direction) from a state in which the X-ray irradiation unit 4 in FIG. 2 is behind the support column 10c (X2 direction). The X-ray detection unit 5 is disposed between the subject 90 and a top plate 13 on which the subject 90 is placed at the time of X-ray irradiation. That is, the X-ray detection unit 5 is disposed at a position between the top plate 13 and a back 90a of the subject 90 by the operator at the time of X-ray irradiation (when the subject 90 is imaged). In the present embodiment, a longitudinal direction of the top plate 13 is set to an X direction. A direction on the side where the head of the subject 90 is disposed is set to the X1 direction, and a direction on the side where the feet are disposed is set to the X2 direction. A lateral direction (the left-right direction of the subject 90) of the top plate 13 orthogonal to the X direction is set to a Y direction. A direction on the right hand side of the subject 90 when the subject 90 lies on his back is set to a Y1 direction, and a direction on the left hand side is set to a Y2 direction. The top plate 13 is a top plate of a bed provided in a hospital room.

In the present embodiment, the projection unit 3 is configured to project the marker 40 in the direction along the optical axis direction of the X-rays radiated from the X-ray irradiation unit 4. Specifically, the projection unit 3 projects the marker 40 onto the imaging position 80 from the Z1 direction in the Z2 direction.

Here, in a case where the subject 90 is imaged by the X-ray imaging apparatus 1, the operator moves the X-ray imaging apparatus 1 to a predetermined position. The operator adjusts relative positions between the X-ray irradiation unit 4, the X-ray detection unit 5, and the subject 90. After the adjustment of the relative positions is completed, the operator captures an X-ray image by performing an operation of radiating X-rays from the X-ray irradiation unit 4. In the present embodiment, the X-ray irradiation unit 4 is configured to be movable by a doctor, a radiologist, or the like. The X-ray detection unit 5 is disposed by a doctor, a radiologist, or the like. Thus, relative positions between the X-ray irradiation unit 4, the X-ray detection unit 5, and the subject 90 may not be appropriate for the imaging conditions 20. In a case where the relative positions between the X-ray irradiation unit 4, the X-ray detection unit 5, and the subject 90 are not appropriate for the imaging conditions 20, image quality of an X-ray image obtained by imaging an imaging part of the subject 90 may deteriorate. A position appropriate for the imaging conditions 20 is a preferable position of the subject 90, which is set according to an imaging part and an imaging direction of the subject 90.

Therefore, in the present embodiment, the projection unit 3 projects, onto the imaging position 80, a marker 40 (refer to FIG. 1) for guiding relative positions between the X-ray irradiation unit 4, the X-ray detection unit 5, and the subject 90 to positions appropriate for the imaging conditions 20 (refer to FIG. 1) before starting imaging (X-ray irradiation) of the subject 90. Specifically, the projection unit 3 is configured to project, onto the imaging position 80 that is subject 90 or the surface 13a to which the subject 90 is fixed, the marker 40 indicating a contour of the subject 90 for guiding a position of the subject 90 to be a target position acquired by the target position acquisition unit 6b (refer to FIG. 1).

Subject Image and Subject Target Image

A subject image 30 and a subject target image 31 will be described with reference to FIGS. 4 and 5.

The subject image 30 illustrated in FIG. 4 is an image captured by the imaging unit 2. Specifically, the subject image 30 is an image indicating a position of the subject 90 who may not be in a position and a posture appropriate for the imaging conditions 20 (refer to FIG. 1). The position information acquisition unit 6a (refer to FIG. 1) is configured to acquire a position and a posture of the subject 90 captured in the subject image 30. In the subject image 30, only the contour line is illustrated as the subject 90, but, actually, the parts (the mouth, the ears, the nose, and the like) of the subject 90 and the clothes worn by the subject 90 are captured. In the example illustrated in FIG. 4, the subject 90 is hatched for convenience in order to distinguish it from an image 36 indicating a target contour line 40a (refer to FIG. 8) that will be described later.

Figure 5:
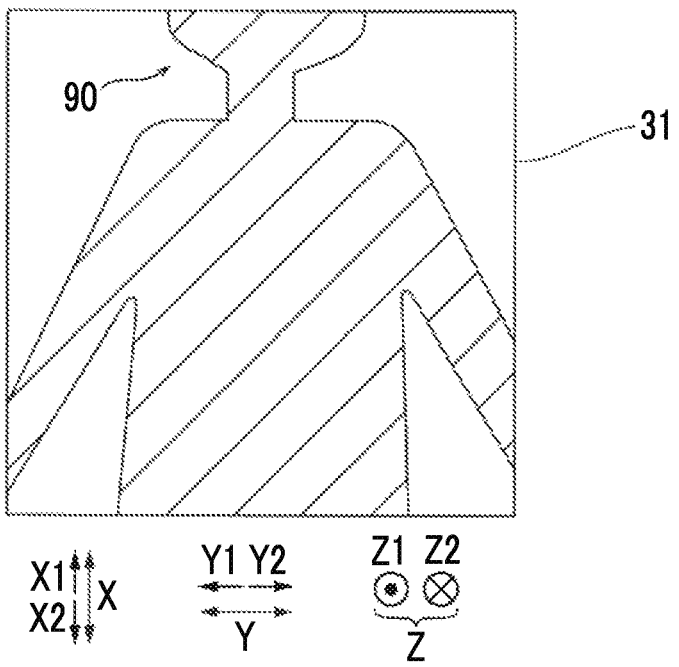
FIG. 5 is a schematic diagram for describing a subject target image in which a subject in a position and a posture appropriate for imaging conditions is captured.

The subject target image 31 illustrated in FIG. 5 is an image in which the subject 90 in a position and a posture appropriate for the imaging conditions 20 is captured. In the present embodiment, the position information acquisition unit 6a, the target position acquisition unit 6b (refer to FIG. 1), and the marker acquisition unit 6c (refer to FIG. 1) acquire the marker (refer to FIG. 1) for guiding the subject to the position and the posture captured in the subject target image 31 on the basis of the subject image 30 captured by the imaging unit 2 (refer to FIG. 1). The parts (the mouth, the ears, the nose, and the like) of the subject 90 and the clothes worn by the subject 90 are also captured in the subject target image 31. Also in the example illustrated in FIG. 5, the subject 90 is hatched for convenience in order to distinguish it from the image 36 indicating the target contour line 40a (refer to FIG. 8) that will be described later.

Specifically, the position information acquisition unit 6a acquires position information of the subject 90 from the subject image 30. The target position acquisition unit 6b acquires a target position and a target posture appropriate for the imaging conditions 20 on the basis of the position information of the subject 90 acquired by the position information acquisition unit 6a and the imaging conditions 20 stored in the storage unit 7 (refer to FIG. 1). The marker acquisition unit 6c acquires the marker 40 for guiding the subject 90 to the target position and the target posture acquired by the target position acquisition unit 6b.

Acquisition of Contour Line and Center Line of Subject

Figure 6:
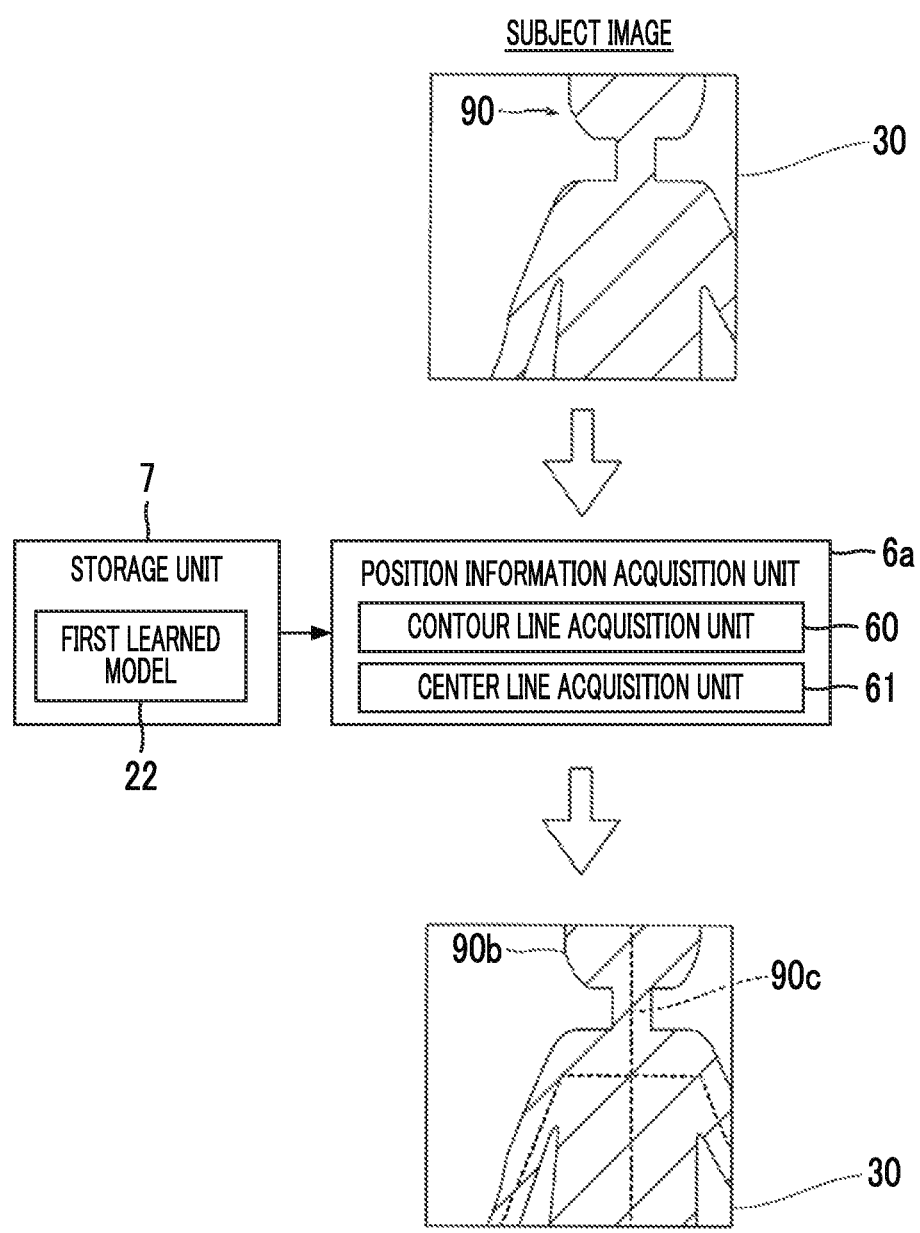
FIG. 6 is a schematic diagram for describing a configuration in which a position information acquisition unit according to the embodiment acquires a contour line and a center line of a subject.

A configuration in which the position information acquisition unit 6a acquires position information of the subject 90 will be described with reference to FIG. 6. In the present embodiment, the position information acquisition unit 6a acquires a contour line 90b and a center line 90c of the subject 90 captured in the subject image 30, and thus acquires position information of the subject 90 captured in the subject image 30. The position information acquisition unit 6a acquires the center line 90c of the subject 90, which is not visible. In the example illustrated in FIG. 6, for convenience, the center line 90c of the subject 90 is indicated by a dashed line.

In the present embodiment, the contour line acquisition unit 60 is configured to acquire the contour line 90b of the subject 90. The center line acquisition unit 61 is configured to acquire the center line 90c of the subject 90.

In the present embodiment, the contour line acquisition unit 60 acquires the contour line 90b of the subject 90 through rule-based image processing. For example, the contour line acquisition unit 60 acquires the contour line 90b of the subject 90 by acquiring a boundary line between the subject 90 and the background through image processing for extracting the boundary line.

The center line acquisition unit 61 is configured to acquire the center line 90c on the basis of the first learned model 22 in which acquisition of the center line 90c of the subject 90 from an image in which the subject 90 is captured has been learned, and the subject image 30. The first learned model 22 is generated by learning a learning model with an image in which the subject 90 is captured as training input data and the center line of the subject 90 as training output data. The generated first learned model 22 is stored in the storage unit 7 in advance.

Acquisition of Target Position and Target Posture

Next, with reference to FIG. 7, a configuration in which the target position acquisition unit 6b acquires a target position and a target posture will be described.

In the present embodiment, the target position acquisition unit 6b is configured to acquire the target position according to the imaging conditions 20 on the basis of the imaging conditions 20 (refer to FIG. 1) and the position information of the subject 90 in the subject image 30. In the present embodiment, the target position acquisition unit 6b is configured to acquire a target posture along with a target position according to the imaging conditions 20 on the basis of the imaging conditions 20, the position information, and posture information of the subject 90.

Figure 7:
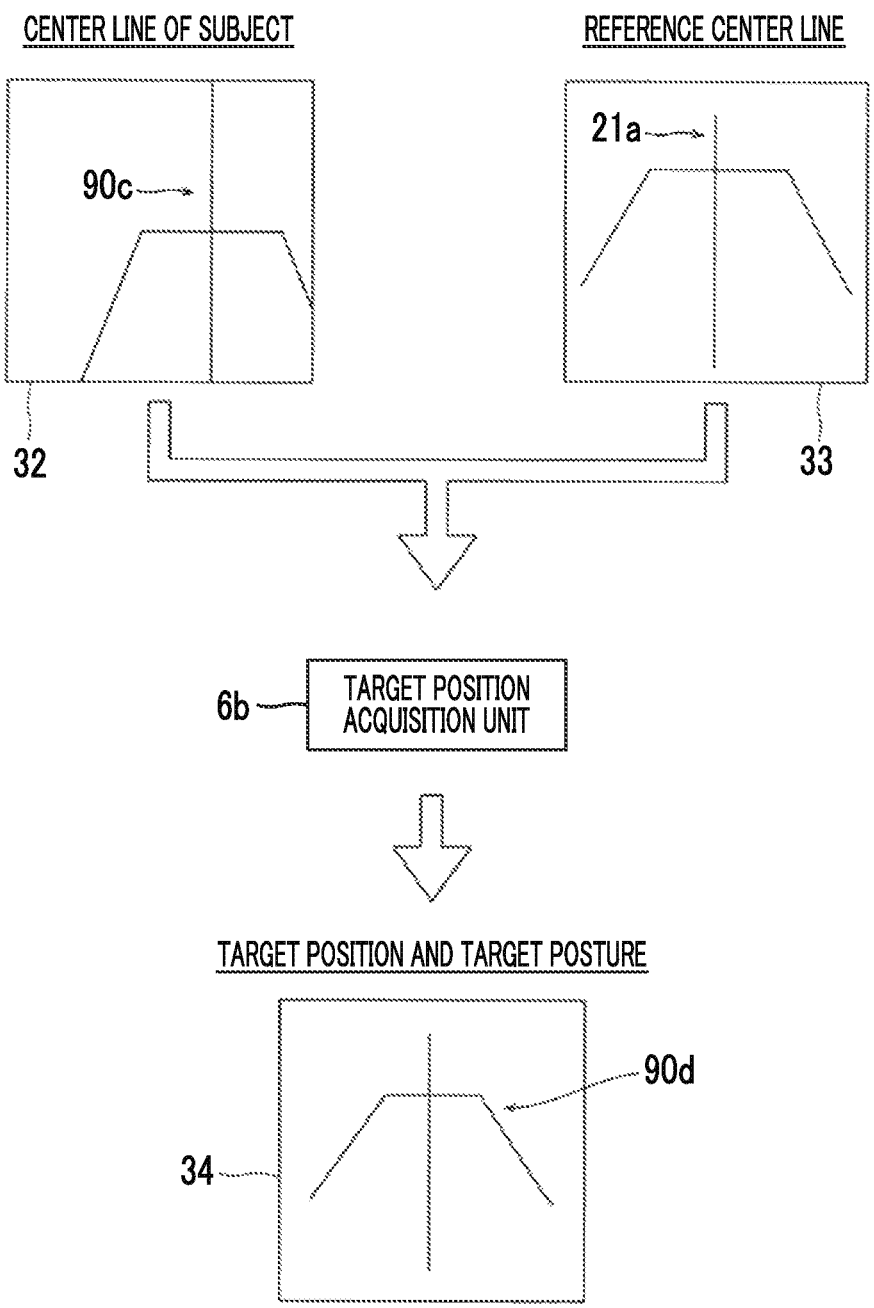
FIG. 7 is a schematic diagram for describing a configuration in which a target position acquisition unit according to the embodiment acquires a target position and a target posture.

Specifically, as illustrated in FIG. 7, the target position acquisition unit 6b is configured to acquire the target position and the target posture on the basis of the center line 90c acquired by the center line acquisition unit 61 (refer to FIG. 1) and the reference center line 21a. Here, the reference center line 21a is a center line representing a position and a posture appropriate for the imaging conditions 20. That is, the reference center line 21a is a center line representing a position and a posture appropriate for the imaging conditions 20 without considering a body shape of the subject 90 or the like. Therefore, in the present embodiment, the target position acquisition unit 6b acquires a center line 90d shown in an image 34 on the basis of a center line 90c shown in an image 32 and the reference center line 21a shown in an image 33. The center line 90d is a center line in a case where a position and a posture of the subject 90 become the target position and the target posture. The image 32, the image 33, and the image 34 are images for describing a configuration in which the target position acquisition unit 6b acquires the target position and the target posture. That is, the image 32, the image 33, and the image 34 are images that are not generated.

In the present embodiment, the target position acquisition unit 6b is configured to acquire a movement direction for moving the subject 90 to the target position on the basis of the position of the subject 90 captured in the subject image 30 and the target position. Specifically, the target position acquisition unit 6b is configured to acquire the movement direction for moving the subject 90 to the target position on the basis of a position of the center line 90d and a position of the center line 90c of the subject 90. More specifically, the target position acquisition unit 6b is configured to acquire the movement direction for moving the subject 90 to the target position by acquiring a difference between the position of the center line 90*d* and the position of the center line 90*c*.

Acquisition of Marker

In the present embodiment, the marker acquisition unit 6*c* configured to acquire, as a marker 40, a target contour line 40*a* when the subject 90 takes the target posture at the target position or the subject target image (refer to FIG. 5) that is an image obtained by converting the subject 90 captured in the subject image 30 (refer to FIG. 3) such that the subject 90 is in the target position and the target posture, on the basis of the subject image 30, the target position, and the target posture.

Acquisition of Target Contour Line

Figure 8:
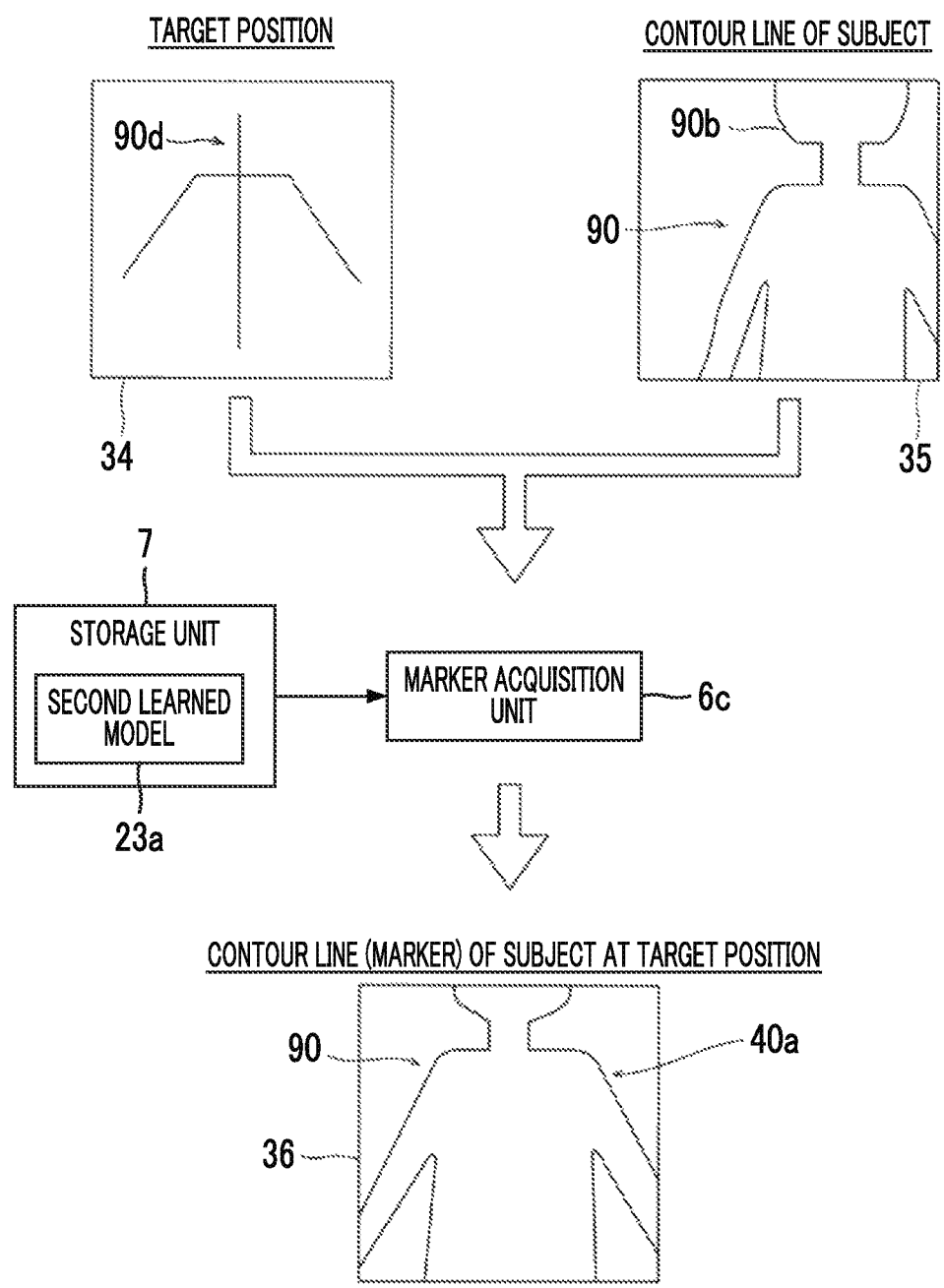
FIG. 8 is a schematic diagram for describing a configuration in which a marker acquisition unit according to the embodiment acquires a target contour line.

First, with reference to FIG. 8, a configuration in which the marker acquisition unit 6*c* acquires the target contour line 40*a* will be described. In the present embodiment, the marker acquisition unit 6*c* is configured to acquire the target contour line 40*a* that is a contour line when the subject 90 takes the target posture at the target position, as the marker 40 (refer to FIG. 1). In the present embodiment, the marker acquisition unit 6*c* is configured to acquire the target contour line 40*a* on the basis of the second learned model 23*a* in which acquisition of the target contour line 40*a* of the subject 90 from the center line 90*c* (refer to FIG. 7) of the subject 90 has been learned, the reference information 21, the target position, and the target posture.

In the present embodiment, the second learned model 23*a* is generated by causing a learning model to learn acquisition of the contour line 90*b* of the subject 90 when the subject 90 takes the target posture at the target position on the basis of the contour line 90*b* (refer to FIG. 6) of the subject 90 captured in the subject image 30 (refer to FIG. 4) and the reference center line 21*a* (refer to FIG. 7). That is, the second learned model 23*a* is generated by learning a learning model with the contour line 90*b* of the subject 90 acquired from the subject image 30 and the reference center line 21*a* as training input data, and a contour line when the subject 90 takes the target posture at the target position as training output data. The generated second learned model 23*a* is stored in the storage unit 7 in advance.

Thus, in the present embodiment, the marker acquisition unit 6*c* inputs the center line 90*d* at the target position shown in the image 34 and the contour line 90*b* of the subject 90 shown in the image 35 into the second learned model 23*a* and thus acquires the target contour line 40*a* shown in the image 36. An image 35 and an image 36 are images for describing a configuration in which the marker acquisition unit 6*c* acquires the target contour line 40*a*. That is, the image 35 and the image 36 are images that are not generated.

In the present embodiment, the marker acquisition unit 6*c* is configured to acquire the target contour line 40*a* having an actual size of the subject 90 as the marker 40. Specifically, the marker acquisition unit 6*c* acquires the target contour line 40*a* that has the actual size of the subject 90 when the target contour line 40*a* are projected onto the imaging position 80 (refer to FIG. 3).

Acquisition of Subject Target Image

Figure 9:
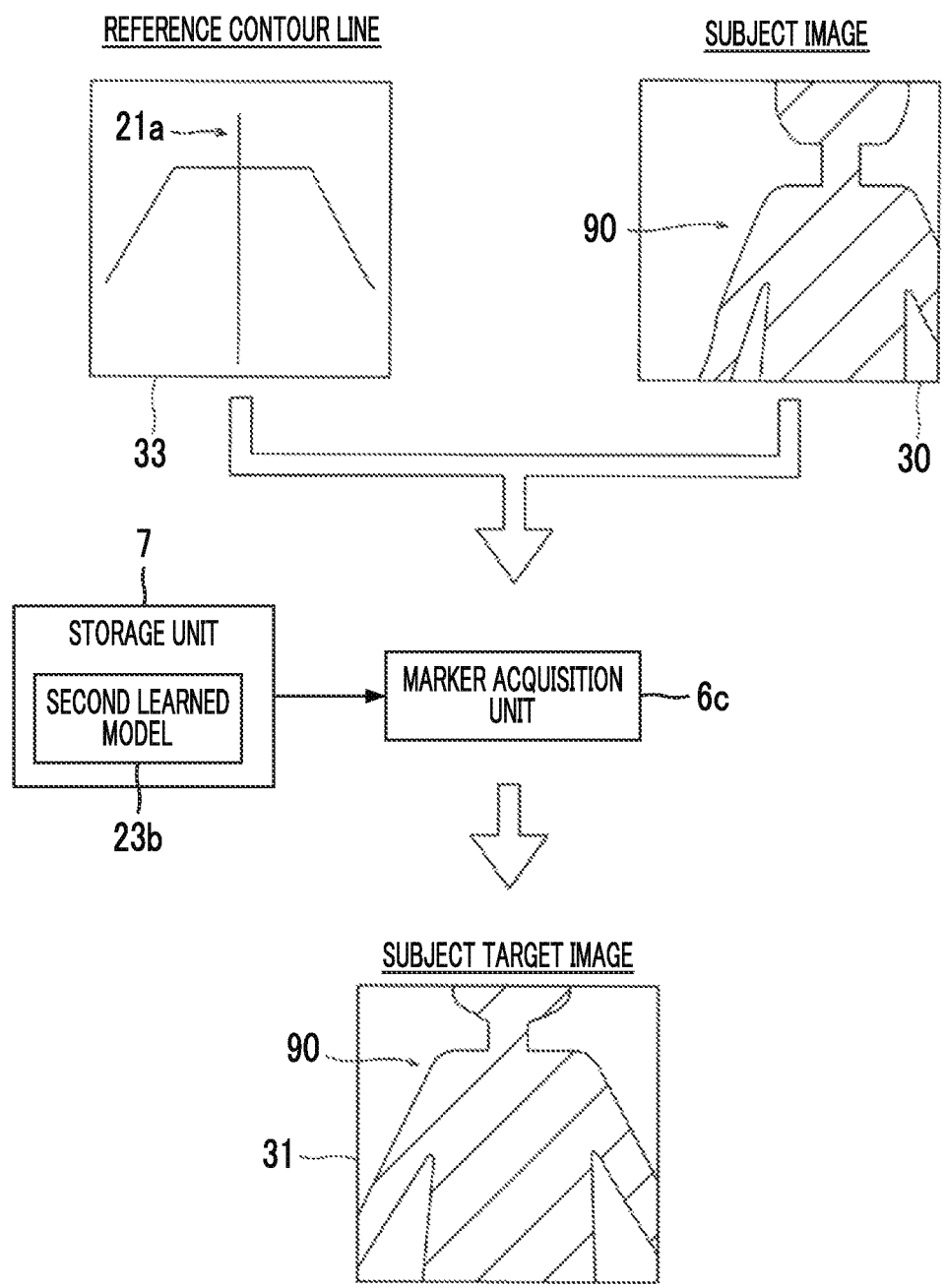
FIG. 9 is a schematic diagram for describing a configuration in which the marker acquisition unit according to the embodiment acquires a subject target image.

Next, with reference to FIG. 9, a configuration in which the marker acquisition unit 6*c* acquires the subject target image 31 will be described. In the present embodiment, the marker acquisition unit 6*c* is configured to acquire the subject target image 31 on the basis of the second learned model 23*b* in which outputting of an image when the subject 90 takes the target posture at the target position has been learned by using an image in which the subject 90 is captured and the reference information 21 (refer to FIG. 1), the reference information 21, the target position, and the target posture. The subject target image 31 is an image generated by converting the subject 90 captured in the subject image 30 such that a position and a posture of the subject 90 become the target position and the target posture.

In the present embodiment, the second learned model 23*b* is generated by causing a learning model to learn outputting of the subject target image 31 that is an image when the subject 90 takes the target posture at the target position on the basis of the subject image 30 (refer to FIG. 4) and the reference center line 21*a* (refer to FIG. 7). That is, the second learned model 23*b* is generated by learning a learning model with the subject image 30 and the reference center line 21*a* as training input data and the image of the subject 90 when the subject 90 takes the target posture at the target position as training output data. The generated second learned model 23*b* is stored in the storage unit 7 in advance.

In the present embodiment, the marker acquisition unit 6*c* acquires either the target contour line 40*a* or the subject target image 31 on the basis of selection of the operator or setting by the operator. That is, in a case where the operator selects or sets acquisition of the target contour line 40*a*, the marker acquisition unit 6*c* acquires the target contour line 40*a* as the marker 40. In a case where the operator selects or sets acquisition of the subject target image 31, the marker acquisition unit 6*c* acquires the subject target image 31 as the marker 40.

Other Markers Acquired by Marker Acquisition Unit

In the present embodiment, the marker acquisition unit 6*c* is configured to acquire a marker 40*b* (refer to FIG. 11) indicating a movement direction of the subject 90 as the marker 40 for guiding the subject 90 to the target position and the target posture. Specifically, the marker acquisition unit 6*c* is configured to acquire the marker 40*b* indicating the movement direction on the basis of the movement direction, acquired by the target position acquisition unit 6*b*, for moving the subject 90 to the target position. The target position acquisition unit 6*b* acquires the movement direction on the basis of a position of the subject 90 (the current position of the subject 90) captured in the subject image 30 (refer to FIG. 4) and the target position.

Other Information Acquired by Marker Acquisition Unit

Figure 10:
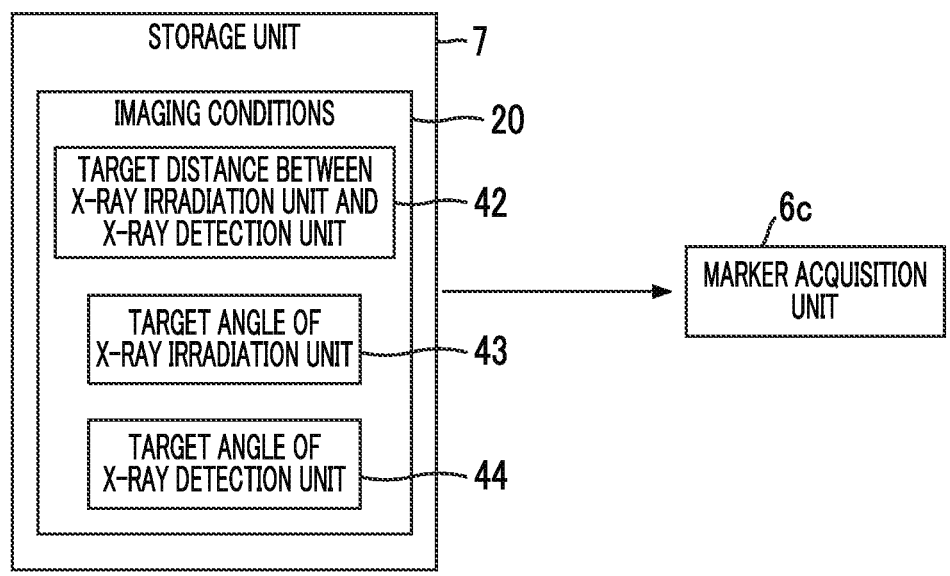
FIG. 10 is a schematic diagram for describing a configuration in which the marker acquisition unit according to the embodiment acquires a target distance between an X-ray irradiation unit and an X-ray detection unit, a target angle of the X-ray irradiation unit, and a target angle of the X-ray detection unit.

As illustrated in FIG. 10, the imaging conditions 20 include not only a position and a posture of the subject 90 but also information regarding a position of the X-ray detection unit 5 (refer to FIG. 1). Therefore, in the present embodiment, the marker acquisition unit 6*c* (refer to FIG. 1) is configured to acquire a target position 41 (refer to FIG. 11) of an X-ray detection region in the X-ray detection unit 5. Specifically, the marker acquisition unit 6*c* acquires the target position 41 of an X-ray detection region on the basis of position information of the X-ray detection region included in the imaging conditions 20.

The imaging conditions 20 also include preferable position information of the X-ray irradiation unit 4 (refer to FIG. 1) and the X-ray detection unit 5. Therefore, in the present embodiment, the marker acquisition unit 6*c* is configured to acquire at least one of a target distance 42 between the X-ray irradiation unit 4 and the X-ray detection unit 5, a target angle 43 of the X-ray irradiation unit 4, and a target angle 44 of the X-ray detection unit 5 on the basis of the preferable position information of the X-ray irradiation unit 4 and the X-ray detection unit 5 included in the imaging conditions 20. In the present embodiment, the marker acquisition unit 6*c* is configured to acquire all of the target distance 42, the target angle 43, and the target angle 44.

(Projected Marker and Information)

Next, the marker 40 and information projected by the projection unit 3 (refer to FIG. 1) will be described with reference to FIG. 11. As illustrated in an image 37 in FIG. 11, the projection unit 3 is configured to project a contour of the subject 90 for guiding a position and a posture of the subject 90 (refer to FIG. 1) to be the target position and the target posture onto the imaging position 80 (refer to FIG. 1) as the marker 40. Specifically, the projection unit 3 is configured to project at least the target contour line 40*a* as the marker 40. More specifically, the projection unit 3 is configured to project the target contour line 40*a* or the subject target image 31 as the marker 40 onto the imaging position 80. In the example illustrated in FIG. 11, the projection unit 3 is configured to project the target contour line 40*a* onto the imaging position 80. The image 37 is an image for describing the marker 40 projected by the projection unit 3. That is, the image 37 is an image that is not generated.

In the present embodiment, the marker acquisition unit 6*c* (refer to FIG. 1) acquires the target contour line 40*a* having an actual size of the subject 90. Therefore, the projection unit 3 is configured to project the target contour line 40*a* having the actual size of the subject 90 onto the imaging position 80.

Figure 11:
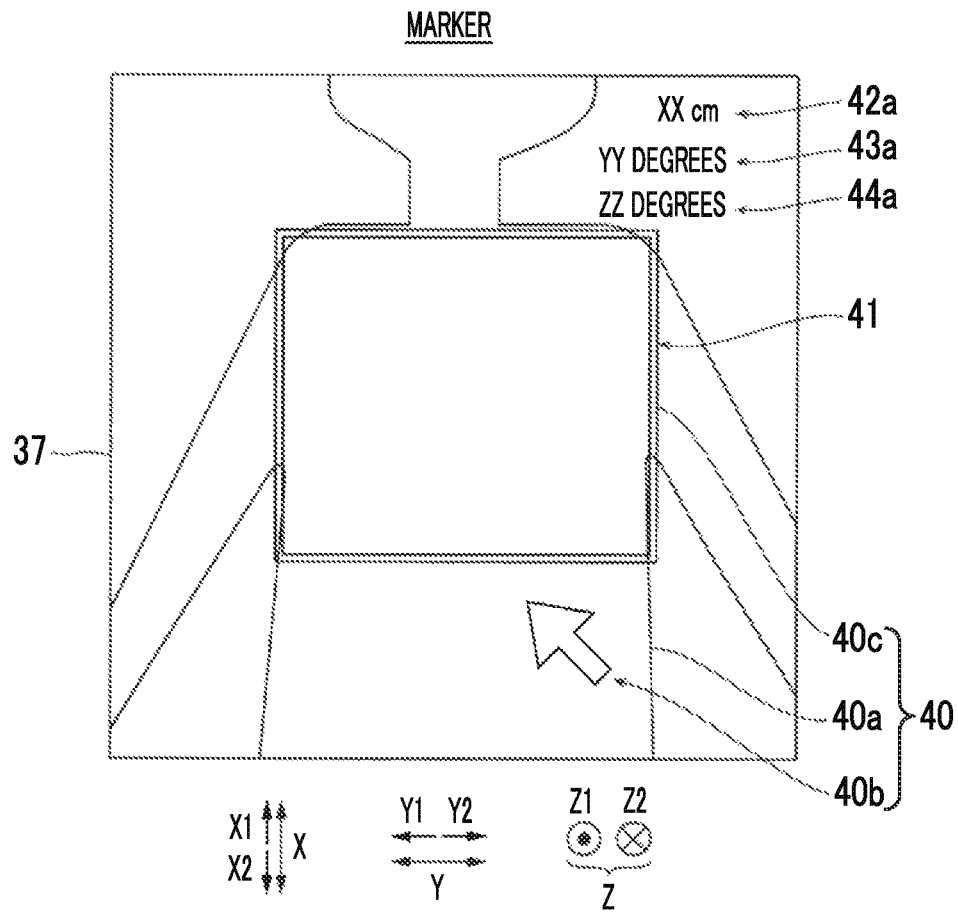
FIG. 11 is a schematic diagram for describing a marker and information projected onto an imaging position by a projection unit according to an embodiment.

As illustrated in FIG. 11, the projection unit 3 is configured to project a marker 40*b* indicating a movement direction of the subject 90. In the example illustrated in FIG. 11, the marker 40*b* indicating the movement direction indicates that the subject 90 is moved to the upper left of the image 37.

In the present embodiment, the projection unit 3 is configured to project a target position 41 of the X-ray detection region onto the imaging position 80. In the present embodiment, the projection unit 3 is configured to display a rectangular marker 40*c* at the position of the X-ray detection region appropriate for the imaging conditions 20 (refer to FIG. 1), to project the target position 41 of the X-ray detection region.

The projection unit 3 is configured to project, onto the imaging position 80, at least one of the target distance 42 between the X-ray irradiation unit 4 and the X-ray detection unit 5, the target angle 43 of the X-ray irradiation unit 4, and the target angle 44 of the X-ray detection unit 5. In the example illustrated in FIG. 11, the projection unit 3 is configured to project all of a target distance 42 between the X-ray irradiation unit 4 and the X-ray detection unit 5, a target angle 43 of the X-ray irradiation unit 4, and a target angle 44 of the X-ray detection unit 5. In the present embodiment, the projection unit 3 projects, as character information, each of the target distance 42 between the X-ray irradiation unit 4 and the X-ray detection unit 5, the target angle 43 of the X-ray irradiation unit 4, and the target angle 44 of the X-ray detection unit 5.

The target distance 42 between the X-ray irradiation unit 4 and the X-ray detection unit 5, the target angle 43 of the X-ray irradiation unit 4, and the target angle 44 of the X-ray detection unit 5 are character information. Therefore, when the projection unit 3 projects the target distance 42 between the X-ray irradiation unit 4 and the X-ray detection unit 5, the target angle 43 of the X-ray irradiation unit 4, and the target angle 44 of the X-ray detection unit 5 onto the imaging position 80, the projection unit 3 projects the target distance 42 between the X-ray irradiation unit 4 and the X-ray detection unit 5, the target angle 43 of the X-ray irradiation unit 4, and the target angle 44 of the X-ray detection unit 5 onto a position where there are few unevennesses. In the present embodiment, the projection unit 3 projects the target distance 42 between the X-ray irradiation unit 4 and the X-ray detection unit 5, the target angle 43 of the X-ray irradiation unit 4, and the target angle 44 of the X-ray detection unit 5 onto, for example, the surface 13*a* (refer to FIG. 3) of the top plate 13 (refer to FIG. 3) in the imaging position 80.

Adjustment of Marker Shape

Here, the imaging position 80 (refer to FIG. 3) includes the body surface of the subject 90 (refer to FIG. 3) and the surface 13*a* (refer to FIG. 3) to which the subject 90 is fixed. Therefore, the projection unit 3 (refer to FIG. 1) projects the marker 40 onto the body surface of the subject 90 and the surface 13*a* to which the subject 90 is fixed. That is, the projection surface onto which the projection unit 3 projects the marker 40 has an uneven shape. In a case where the marker 40 is projected onto a projection surface having an uneven shape, the shape of the marker 40 may be deformed because a distance from the projection unit 3 to each projection position changes. Therefore, the projection unit 3 is configured to project the marker 40 of which a shape is adjusted on the basis of the projection distance onto the imaging position 80.

In the present embodiment, the marker shape adjustment unit 6*d* (refer to FIG. 1) is configured to adjust a shape of the marker 40 on the basis of a projection distance acquired by the projection distance acquisition unit 8 (refer to FIG. 1).

Figure 12:
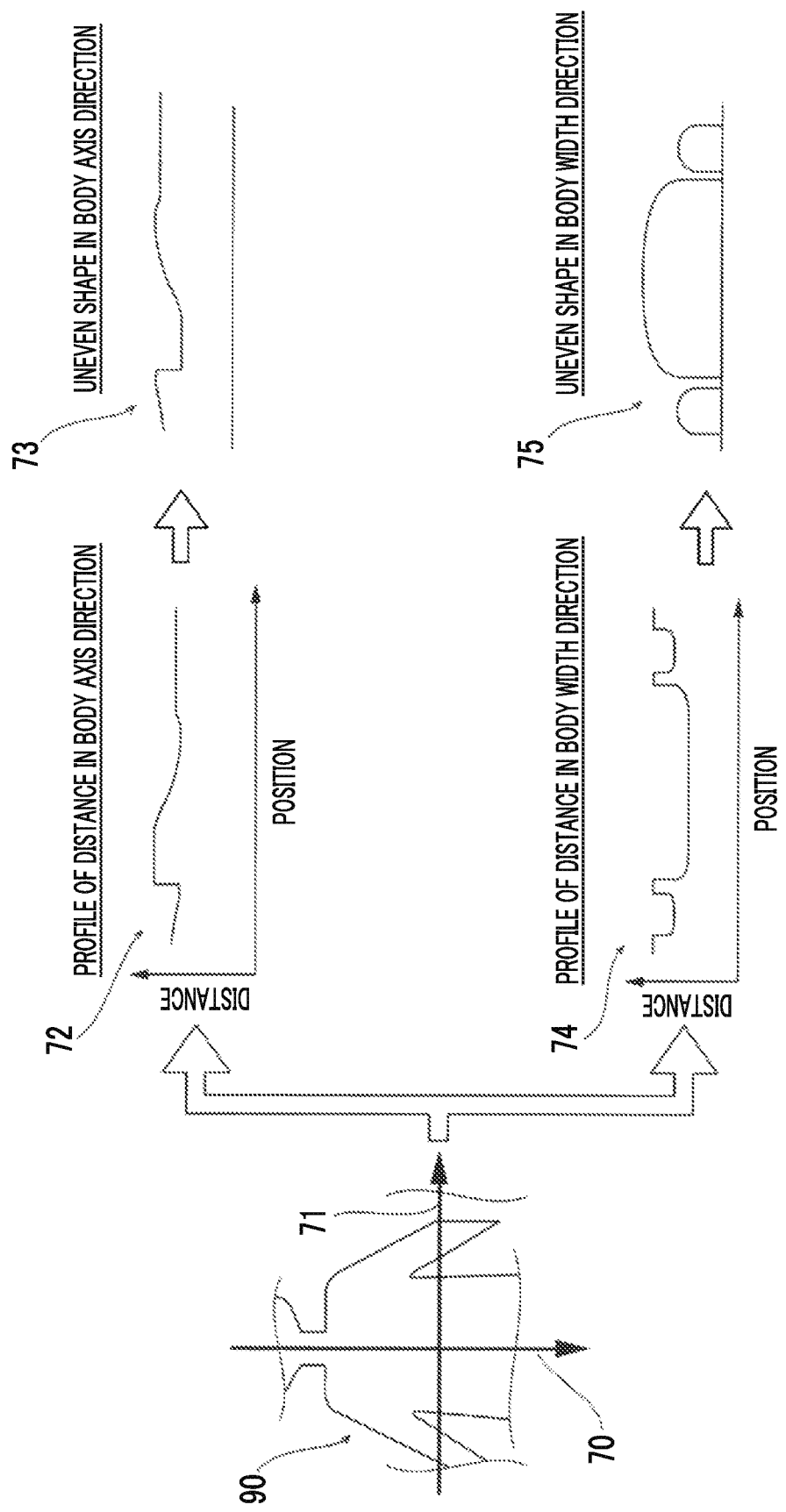
FIG. 12 is a schematic diagram for describing a configuration in which a projection distance acquisition unit according to the embodiment acquires a projection distance.

As illustrated in FIG. 12, the projection distance acquisition unit 8 (refer to FIG. 1) acquires a projection distance that is a distance from the projection unit 3 (refer to FIG. 3) to the imaging position 80 (refer to FIG. 3) along a body axis direction (X direction) of the subject 90 as indicated by an arrow 70. As indicated by an arrow 71, the projection distance acquisition unit 8 acquires a projection distance that is a distance from the projection unit 3 to the imaging position 80 along a body width direction (Y direction) of the subject 90.

A graph 72 is a graph indicating a change in the projection distance in the body axis direction at a predetermined position. In the graph 72, the horizontal axis expresses a position and the vertical axis expresses a distance. Regarding the projection distance in the body axis direction indicated in the graph 72, the projection distance acquisition unit 8 acquires a distance to the body surface of the subject 90 from the projection unit 3 in the direction from the head to the chest along the body axis of the subject 90. The graph 72 indicates that, as the projection distance increases, the distance from the projection unit 3 to the body surface of the subject 90 increases. The graph 72 indicates that, as the projection distance decreases, the distance from the projection unit 3 to the body surface of the subject 90 decreases.

In the present embodiment, the marker shape adjustment unit 6*d* acquires an uneven shape 73 of the subject 90 in the body axis direction on the basis of the graph 72. Specifically, the marker shape adjustment unit 6*d* acquires the uneven shape 73 of the subject 90 in the body axis direction by acquiring an amount of protrusion from the surface 13*a* of the top plate 13 on the basis of the distance in the graph 72. The marker shape adjustment unit 6*d* acquires the uneven shape 73 of the subject 90 in the body axis direction while scanning a position where the graph 72 is acquired in the body width direction, and thus acquires the uneven shape 73 of the subject 90 in the body axis direction at the imaging position 80.

A graph 74 is a graph indicating a change in the projection distance in the body width direction at a predetermined position. In the graph 74, the horizontal axis expresses a position and the vertical axis expresses a distance. The marker shape adjustment unit 6*d* acquires an uneven shape 75 of the subject 90 in the body width direction on the basis of the graph 74. The graph 74 is the same graph as the graph 72 except that directions in which the projection distance is acquired are different. The marker shape adjustment unit 6*d* acquires the uneven shape 75 of the subject 90 in the body width direction while scanning a position where the graph 74 is acquired in the body axis direction, and thus acquires the uneven shape 75 of the subject 90 in the body width direction at the imaging position 80. The configuration in which the marker shape adjustment unit 6*d* acquires the uneven shape 75 of the subject 90 in the body width direction on the basis of the graph 74 is the same as the configuration in which the marker shape adjustment unit 6*d* acquires the uneven shape 73 of the subject 90 in the body axis direction on the basis of the graph 72, and thus detailed description thereof will be omitted.

The marker shape adjustment unit 6*d* adjusts a shape of the marker 40 on the basis of the uneven shape 73 of the subject 90 in the body axis direction and the uneven shape 75 of the subject 90 in the body width direction. Specifically, the marker shape adjustment unit 6*d* acquires the uneven shape 73 in the body axis direction and the uneven shape 75 in the body width direction in a surface of the imaging position 80, and acquires an uneven shape of the imaging position 80. The marker shape adjustment unit 6*d* adjusts the shape of the marker 40 on the basis of the uneven shape of the imaging position 80 and a distance from the projection unit 3 to each imaging position 80 such that the shape of the marker 40 is not deformed. Specifically, the marker shape adjustment unit 6*d* adjusts the shape of the marker 40 by adjusting an enlargement ratio on the basis of the projection distance for each pixel of an image projected as the marker 40.

Notification Based on Target Contour Line

Next, with reference to FIG. 13, a configuration in which the notification unit 6*e* performs a notification will be described. In the present embodiment, the notification unit 6*e* is configured to make display modes of the marker 40 different between before and after a position and a posture of the subject 90 become the target position and the target posture. Specifically, the notification unit 6*e* is configured to perform a notification by making display modes of the target contour line 40*a* different before and after the position and the posture of the subject 90 become the target position and the target posture.

In the present embodiment, the notification unit 6*e* notifies that the position and the posture of the subject 90 become the target position and the target posture by making colors of the target contour line 40*a* different before and after the position and the posture of the subject 90 become the target position and the target posture. For example, the notification unit 6*e* displays the target contour line 40*a* red before the position and the posture of the subject 90 become the target position and the target posture. The notification unit 6*e* displays the target contour line 40*a* green after the position and the posture of the subject 90 become the target position and the target posture. The example illustrated in FIG. 13 is an example of making display modes (display colors) of the target contour line 40*a* (marker 40) different by making a thickness of the target contour line 40*a* in the image 37*a* indicating a state in which the position and the posture of the subject 90 have not become the target position and the target posture different from a thickness of the target contour line 40*a* in an image 37*b* indicating a state in which the position and the posture of the subject 90 become the target position and the target posture. The images 37*a* and 37*b* are images for describing a configuration in which the notification unit 6*e* performs a notification, and are not images generated by the X-ray imaging apparatus 1.

Marker Projection Process

Figure 14:
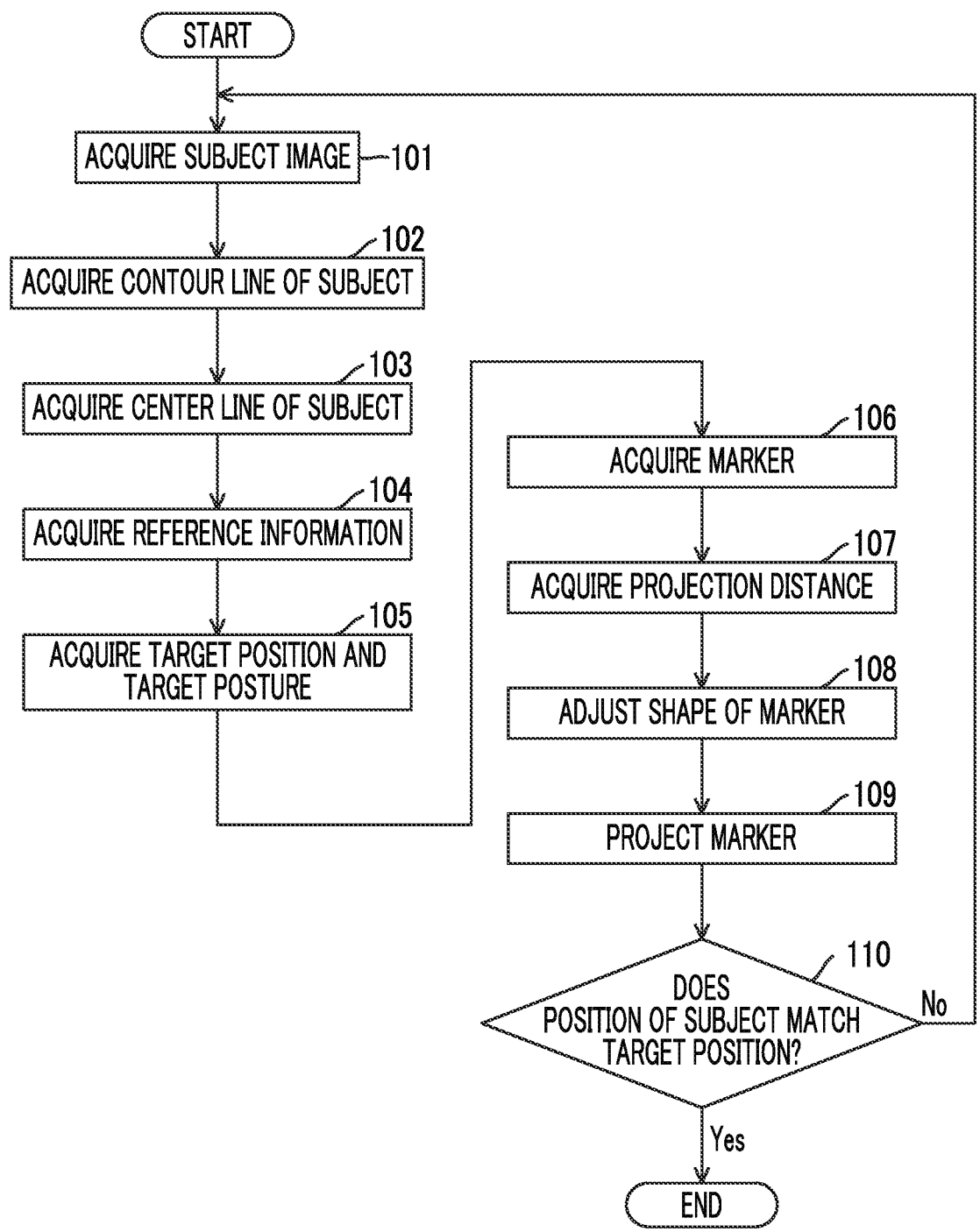
FIG. 14 is a flowchart for describing a process in which the X-ray imaging apparatus according to the embodiment projects a marker.

Next, with reference to FIG. 14, a process will be described in which the control unit 6 (refer to FIG. 1) acquires the marker 40 (refer to FIG. 1) and the projection unit 3 (refer to FIG. 1) projects the marker 40 (refer to FIG. 1) onto the imaging position 80 (refer to FIG. 3). The process of projecting the marker 40 illustrated in FIG. 14 is started when an operator selects the imaging conditions 20 (refer to FIG. 1), and is finished when a position and a posture of the subject 90 (refer to FIG. 3) become the target position and the target posture. That is, the process of projecting the marker 40 according to the present embodiment is executed in real time.

In step 101, the control unit 6 acquires the subject image 30 (refer to FIG. 4). Specifically, the control unit 6 acquires the subject image 30 captured by the imaging unit 2 (refer to FIG. 1).

In step 102, the contour line acquisition unit 60 (control unit 6) acquires the contour line 90*b* (refer to FIG. 6) of the subject 90 captured in the subject image 30. In the present embodiment, the contour line acquisition unit 60 acquires the contour line 90*b* through rule-based image processing.

In step 103, the center line acquisition unit 61 (control unit 6) acquires the center line 90*c* (refer to FIG. 6) of the subject 90 captured in the subject image 30. In the present embodiment, the center line acquisition unit 61 acquires the center line 90*c* by using the first learned model 22 (refer to FIG. 1).

In step 104, the target position acquisition unit 6*b* (control unit 6) acquires the reference information 21 stored in the storage unit 7. Specifically, the target position acquisition unit 6*b* acquires the reference center line 21*a* (refer to FIG. 7) as the reference information 21.

In step 105, the target position acquisition unit 6*b* acquires the target position and the target posture. Specifically, the target position acquisition unit 6*b* acquires the center line 90*d* (refer to FIG. 7) of the subject 90 when the subject 90 takes the target posture at the target position on the basis of the center line 90*c* of the subject 90 and the reference center line 21*a*.

In step 106, the marker acquisition unit 6*c* (control unit 6) acquires the marker 40 (refer to FIG. 1). In the present embodiment, the marker acquisition unit 6*c* acquires the target contour line 40*a*, the marker 40*b* indicating a movement direction of the subject 90, the target position 41 of the X-ray detection region, the target distance 42 between the X-ray irradiation unit 4 and the X-ray detection unit 5, the target angle 43 of the X-ray irradiation unit 4, and the target angle 44 of the X-ray detection unit 5.

In step 107, the projection distance acquisition unit 8 acquires projection distances. In the present embodiment, as illustrated in FIG. 12, the projection distance acquisition unit 8 acquires the projection distance of the subject 90 in the body axis direction and the projection distance of the subject 90 in the body width direction.

In step 108, the marker shape adjustment unit 6*d* (control unit 6) adjusts the shape of the marker 40 (refer to FIG. 1) on the basis of the projection distance.

In step 109, the projection unit 3 projects the marker 40 onto the imaging position 80. In the present embodiment, the projection unit 3 projects the target contour line 40*a* (refer to FIG. 8) as the marker 40 onto the imaging position 80. In the present embodiment, as illustrated in FIG. 11, the projection unit 3 projects the marker 40b indicating a movement direction of the subject 90, the target position 41 of the X-ray detection region, the target distance 42 between the X-ray irradiation unit 4 and the X-ray detection unit 5, the target angle 43 of the X-ray irradiation unit 4, and the target angle 44 of the X-ray detection unit 5 onto the imaging position 80.

In step 110, the control unit 6 determines whether or not a position and a posture of the subject 90 become the target position and the target posture. Specifically, the control unit 6 determines whether or not the center line 90c (refer to FIG. 6) of the subject 90 matches the center line 90d (refer to FIG. 7) at the target position and the target posture, and thus determines whether or not the position and the posture of the subject 90 become the target position and the target posture. In a case where the position and the posture of the subject 90 have not become the target position and the target posture, the process proceeds to step 101. In a case where the position and the posture of the subject 90 become the target position and the target posture, the process is finished.

Any of the processes of steps 5102 to 5104 may be performed first.

In the present embodiment, the control unit 6 and the projection unit 3 perform the processes in steps S101 to S110 in real time and project the marker 40. In other words, the control unit 6 and the projection unit 3 are configured to project the marker 40 as a moving image. The subject image 30 is also captured by the imaging unit 2 in real time. That is, the imaging unit 2 captures the subject image 30 as a moving image.

Notification Process

Figure 15:
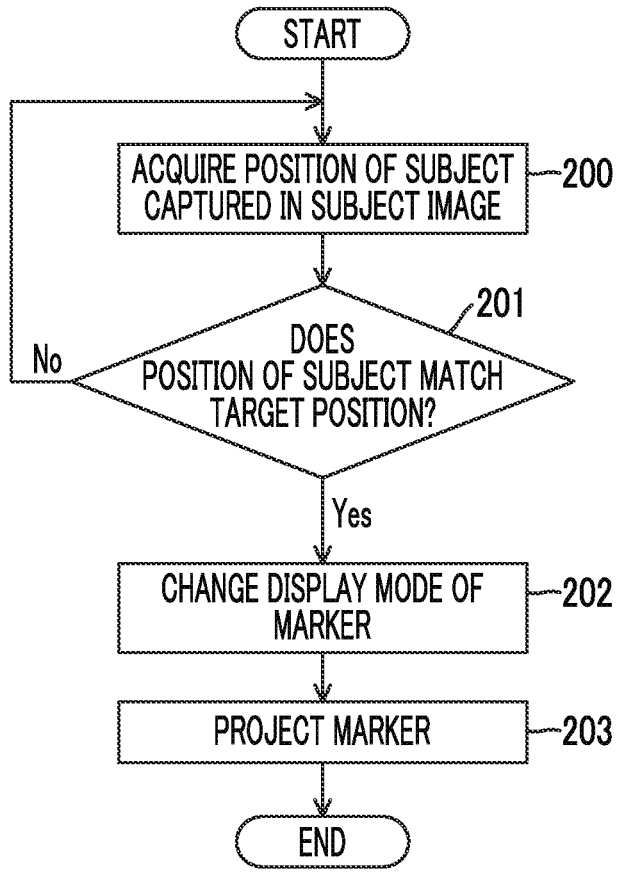
FIG. 15 is a flowchart for describing a process in which the notification unit according to the embodiment notifies that a position and a posture of the subject become the target position and the target posture.

Next, with reference to FIG. 15, a notification process by the notification unit 6e (refer to FIG. 1) will be described. The notification process by the notification unit 6e is started when the first step 109 in the projection process for the marker 40 illustrated in FIG. 14 is performed. That is, the notification process by the notification unit 6e is started when the marker 40 is projected from the projection unit 3.

In step 200, the position information acquisition unit 6a (control unit 6) acquires position information of the subject 90 (refer to FIG. 3) captured in the subject image 30 (refer to FIG. 4). Specifically, the position information acquisition unit 6a acquires the center line 90c (refer to FIG. 6) of the subject 90 captured in the subject image 30.

In step 201, the control unit 6 determines whether or not the position and the posture of the subject 90 become the target position and the target posture. Specifically, the control unit 6 determines whether or not the center line 90c of the subject 90 matches the center line 90d (refer to FIG. 7) at the target position and the target posture and thus determines whether or not the position and the posture of the subject 90 become the target position and the target posture. In a case where the position and the posture of the subject 90 have not become the target position and the target posture, the process proceeds to step 200. In a case where the position and the posture of the subject 90 become the target position and the target posture, the process proceeds to step 202.

In step 202, the notification unit 6e (control unit 6) makes display modes of the marker 40 different. In the present embodiment, as illustrated in FIG. 13, the notification unit 6e makes display modes of the target contour line 40a different by changing a color of the target contour line 40a. In the present embodiment, the notification unit 6e changes the color of the target contour line 40a from red to green.

In step 203, the projection unit 3 projects the marker 40 (target contour line 40a) having different display modes onto the imaging position 80 (refer to FIG. 3). Thereafter, the process is finished.

When the process in step 200 is performed, the marker 40 may be captured in the subject image 30 depending on a timing of imaging each frame of the subject image 30 and a timing of projecting the marker 40 onto the imaging position 80. In this case, the position information acquisition unit 6a acquires the marker 40 projected at a timing at which each frame of the subject image 30 is acquired. The position information acquisition unit 6a removes the marker 40 in each frame of the subject image 30 by subtracting the acquired marker 40 from each frame of the subject image 30. Consequently, the position information acquisition unit 6a can acquire the center line 90c of the subject 90 on the basis of each frame of the subject image 30 from which the marker 40 has been removed. In a case where the marker 40 is not projected at a timing of imaging each frame of the subject image 30, the marker 40 is not captured in each frame of the subject image 30. In this case, the position information acquisition unit 6a may acquire the center line 90c of the subject 90 on the basis of each frame of the acquired subject image 30.

Effects of Present Embodiment

In the present embodiment, the following effects can be achieved.

In the present embodiment, as described above, the X-ray imaging system 100 includes the X-ray irradiation unit 4 that irradiates the subject 90 with X-rays; the X-ray detection unit 5 that detects the X-rays radiated from the X-ray irradiation unit 4; the imaging unit 2 that acquires the subject image 30 obtained by imaging an appearance of the subject 90; the position information acquisition unit 6a that acquires position information of the subject 90 captured in the subject image 30 on the basis of the subject image 30; the target position acquisition unit 6b that acquires a target position according to the imaging conditions 20 on the basis of the imaging conditions 20 and the position information; and the projection unit 3 that projects the marker 40 indicating a contour of the subject 90 for guiding a position of the subject 90 to be the target position acquired by the target position acquisition unit 6b onto the imaging position 80 that is subject 90 or the surface 13a to which the subject 90 is fixed.

Consequently, the marker 40 indicating a contour of the subject 90 for guiding a position of the subject 90 to be the target position is projected onto the imaging position 80, and thus an operator can adjust relative positions between the X-ray irradiation unit 4, the X-ray detection unit 5, and the subject 90 while checking the marker 40 projected on the imaging position 80. That is, the operator can adjust the relative positions between the X-ray irradiation unit 4, the X-ray detection unit 5, and the subject 90 without moving the line of sight from the subject 90. As a result, it is possible to provide the X-ray imaging system 100 capable of suppressing a decrease in the efficiency of relative position adjustment by suppressing the operator from moving the line of sight.

Since the projection unit 3 projecting the marker 40 is provided, the marker 40 for guiding the position of the subject 90 is projected, and thus relative positions between the X-ray irradiation unit 4, the X-ray detection unit 5, and the subject 90 can be adjusted to appropriate positions regardless of a skill level of the operator. Since the projection unit 3 projecting the marker 40 is provided, the operator can check whether relative positions between the X-ray irradiation unit 4, the X-ray detection unit 5, and the subject 90 are appropriate before performing X-ray imaging. As a result, it is possible to suppress re-imaging due to inappropriate relative positions between the X-ray irradiation unit 4, the X-ray detection unit 5, and the subject 90, and thus to suppress an increase an exposure dose of the subject 90 due to the re-imaging.

In the present embodiment, as described above, the X-ray imaging apparatus 1 includes the X-ray irradiation unit 4 that irradiates the subject 90 with X-rays; the X-ray detection unit 5 that detects the X-rays radiated from the X-ray irradiation unit 4; the imaging unit 2 that acquires the subject image 30 obtained by imaging an appearance of the subject 90; the position information acquisition unit 6a that acquires position information of the subject 90 captured in the subject image 30 on the basis of the subject image 30; the target position acquisition unit 6b that acquires a target position according to the imaging conditions 20 on the basis of the imaging conditions 20 and the position information; and the projection unit 3 that projects the marker 40 indicating a contour of the subject 90 for guiding a position of the subject 90 to be the target position acquired by the target position acquisition unit 6b onto the imaging position 80 that is subject 90 or the surface 13a to which the subject 90 is fixed.

Consequently, similarly to the X-ray imaging system 100, it is possible to provide the X-ray imaging apparatus 1 capable of suppressing a decrease in the efficiency of relative position adjustment by suppressing the operator from moving the line of sight.

In the above embodiment, the following further effects can be achieved through following configuration.

That is, in the present embodiment, as described above, the target position acquisition unit 6b is configured to acquire a target posture along with a target position according to the imaging conditions 20 on the basis of the imaging conditions 20, the position information, and posture information of the subject 90, and the projection unit 3 is configured to project a contour of the subject 90 for guiding a position and a posture of the subject 90 to be the target position and the target posture onto the imaging position 80 as the marker 40. Consequently, the position and the posture of the subject 90 are aligned with the marker 40, and thus the position of the subject 90 can be aligned such that a position and a posture appropriate for the imaging conditions 20 can be obtained. That is, even in a case where the skill level of the operator, is low, the position and the posture of the subject 90 can be easily adjusted to a position and a posture appropriate for the imaging conditions 20. As a result, regardless of the skill level of the operator, it is possible to suppress imaging in a state in which the position and the posture of the subject 90 are not appropriate for the imaging conditions 20, and thus to suppress re-imaging.

In the present embodiment, as described above, the marker acquisition unit 6c acquiring the marker 40 is further provided, and the marker acquisition unit 6c is configured to acquire the target contour line 40a that is a contour line when the subject 90 takes the target posture at the target position as the marker 40, and the projection unit 3 is configured to project at least the target contour line 40a as the marker 40. Consequently, the subject 90 is disposed at the position of the target contour line 40a, and thus the position and the posture of the subject 90 can be set to a position and a posture appropriate for the imaging conditions 20. Consequently, for example, unlike a configuration in which a marker having a cross shape is projected at a target position, not only a position of the subject 90 but also a posture thereof can be easily adjusted to a posture appropriate for the imaging conditions 20.

In the present embodiment, as described above, the marker acquisition unit 6c is configured to acquire the target contour line 40a having an actual size of the subject 90 as the marker 40, and the projection unit 3 is configured to project the target contour line 40a having the actual size of the subject 90 onto the imaging position 80. Here, for example, when the position and the posture of the subject 90 are adjusted while checking the target position and the target posture displayed on a monitor, the monitor displays the target position and the target posture in a reduced state. Therefore, there is a difference between a movement distance on the monitor and an actual movement distance. Thus, the efficiency of adjusting the position and the posture of the subject 90 is reduced. Therefore, as described above, since a size of the target contour line 40a is the actual size of the subject 90 by projecting the target contour line 40a having the actual size of the subject 90 onto the imaging position 80, the position and the posture of the subject 90 are adjusted such that the subject 90 approaches the target contour line 40a, and thus the position and the posture of the subject 90 can be set to the target position and the target posture. Consequently, for example, the efficiency of adjusting the position and the posture of the subject 90 can be further improved compared with a configuration in which a relative position is adjusted while checking the target position and the target posture displayed on the monitor.

In the present embodiment, as described above, the position information acquisition unit 6a includes the contour line acquisition unit 60 that acquires the contour line 90b of the subject 90 on the basis of the subject image 30, and the center line acquisition unit 61 that acquires the center line 90c of the subject 90 captured in the subject image 30; the X-ray imaging apparatus 1 further includes the storage unit 7 that stores the reference information 21 that is information regarding a reference position and a reference posture according to the imaging conditions 20. The reference information 21 includes the reference center line 21a that is the center line 90c of the subject 90 when the reference position and the reference posture are taken, and the target position acquisition unit 6b is configured to acquire the target position and the target posture on the basis of the center line 90c acquired by the center line acquisition unit 61 and the reference center line 21a. Consequently, the target position and the target posture are acquired on the basis of the center line 90c of the subject 90 acquired from the subject image 30 and the reference center line 21a, and thus the target position and the target posture can be easily acquired by acquiring the subject image 30.

In the present embodiment, as described above, the center line acquisition unit 61 is configured to acquire the center line 90c on the basis of the first learned model 22 in which acquisition of the center line 90c of the subject 90 from the image in which the subject 90 is captured has been learned, and the subject image 30. Here, for example, in a case where a physique of the subject 90 is large, or depending on a position of the subject 90 in the subject image 30, a unit of the contour of the subject captured in the subject image 30, which cannot be extracted, may be included. In that case, it may be difficult to acquire the center line 90c in a configuration in which contour lines of the subject 90 are extracted and the center of the opposite contour lines is acquired to acquire the center line 90c as image processing. Therefore, as described above, the center line 90c of the subject 90 is acquired by using the first learned model 22 in which acquisition of the center line 90c of the subject 90 from the image in which the subject 90 is captured has been learned. Thus, the center line 90c of the subject 90 can be acquired by using the first learned model 22 regardless of a physique of the subject 90 or a position of the subject 90 captured in the subject image 30.

In the present embodiment, as described above, the marker acquisition unit 6c is configured to acquire, as the marker 40, the target contour line 40a when the subject 90 takes the target posture at the target position or the subject target image 31 that is an image obtained by converting the subject 90 captured in the subject image 30 such that the subject 90 has the target position and the target posture, on the basis of the subject image 30, the target position, and the target posture. The projection unit 3 is configured to project the target contour line 40a or the subject target image 31 as the marker 40 onto the imaging position 80. Consequently, the operator can recognize the marker 40 indicating the target posture at the target position regardless of whether the target contour line 40a or the subject target image 31 is projected. As a result, the operator can easily recognize a position and a posture of the subject 90 appropriate for the imaging conditions 20 regardless of whether the target contour line 40a or the subject target image 31 is projected.

In the present embodiment, as described above, the marker acquisition unit 6c is configured to acquire the target contour line 40a of the subject 90 from the center line 90c of the subject 90, or is configured to acquire the target contour line 40a or the subject target image 31 on the basis of the second learned model (the second learned model 23a or the second learned model 23b) in which outputting of an image when the subject 90 takes the target posture at the target position has been learned by using an image in which the subject 90 is captured and the reference information 21, the reference information 21, the target position, and the target posture. Consequently, since the target contour line 40a is acquired on the basis of the center line 90c acquired from the subject image 30 in which the subject 90 is captured, the target contour line 40a can be acquired according to a body shape of the subject 90 compared with a case where the target contour line 40a is acquired by using the reference center line 21a. Since the image (subject target image 31) when the subject 90 takes the target posture at the target position is acquired on the basis of the image in which the subject is captured and the reference information 21, the subject target image 31 is an image equivalent to the image captured when the subject 90 takes the target posture at the target position. Therefore, even in a case where the target contour line 40a is projected onto the imaging position 80 or the subject target image 31 is projected onto the imaging position 80, the marker 40 can be projected onto the imaging position 80 according to a body shape of the subject 90, and thus a position and a posture of the subject 90 can be easily adjusted.

In the present embodiment, as described above, the target position acquisition unit 6b is configured to acquire a movement direction for moving the subject 90 to the target position on the basis of the position of the subject 90 captured in the subject image 30 and the target position. The marker acquisition unit 6c is configured to acquire the marker 40b indicating the movement direction, and the projection unit 3 is configured to project the marker 40b indicating the movement direction. Consequently, the subject 90 can be easily brought closer to the target position by moving the subject 90 in a direction of the marker 40b indicating the movement direction.

In the present embodiment, as described above, the marker acquisition unit 6c is configured to acquire the target position 41 of the X-ray detection region in the X-ray detection unit 5, and the projection unit 3 is configured to project the target position 41 of the X-ray detection region onto the imaging position 80. Consequently, it is possible to easily understand an appropriate disposition of the X-ray detection unit 5 by checking the target position 41 of the X-ray detection region projected onto the imaging position 80. As a result, the X-ray detection unit 5 can be easily disposed at an appropriate position.

In the present embodiment, as described above, the marker acquisition unit 6c is configured to acquire at least one of the target distance 42 between the X-ray irradiation unit 4 and the X-ray detection unit 5, the target angle 43 of the X-ray irradiation unit 4, and the target angle 44 of the X-ray detection unit 5, and the projection unit 3 is configured to project at least one of the target distance 42 between the X-ray irradiation unit 4 and the X-ray detection unit 5, the target angle 43 of the X-ray irradiation unit 4, and the target angle 44 of the X-ray detection unit 5 onto the imaging position 80. Consequently, it is possible to understand a position and an angle of the X-ray irradiation unit 4 and an angle of the X-ray detection unit 5 appropriate for the imaging conditions 20 by checking the target distance 42 between the X-ray irradiation unit 4 and the X-ray detection unit 5, the target angle 43 of the X-ray irradiation unit 4, and the target angle 44 of the X-ray detection unit 5 projected on the imaging position 80. As a result, regardless of the skill level of the operator, the operator can easily understand whether the X-ray irradiation unit 4 is disposed at a position and an angle appropriate for the imaging conditions 20, and the X-ray detection unit 5 is disposed at an angle appropriate for the imaging conditions 20.

In the present embodiment, as described above, the X-ray imaging apparatus 1 further includes the projection distance acquisition unit 8 that acquires a projection distance that is the distance 50 between the projection unit 3 and the subject 90, or the distance 51 between the projection unit 3 and the surface 13a to which the subject 90 is fixed, and the marker shape adjustment unit 6d that adjusts a shape of the marker 40 on the basis of the projection distance acquired by the projection distance acquisition unit 8. The projection unit 3 is configured to project the marker 40 of which the shape has been adjusted on the basis of the projection distance onto the imaging position 80. Consequently, even in a case where a surface on which the marker 40 is projected has an uneven shape, such as projecting the marker 40 over both the body surface of the subject 90 and the surface 13a to which the subject 90 is fixed, it is possible to suppress the shape of the marker 40 from being deformed. Consequently, the marker 40 for guiding the position and the posture of the subject 90 to be the target position and the target posture can be projected in an appropriate shape.

In the present embodiment, as described above, the X-ray imaging apparatus 1 further includes the notification unit 6e that performs a notification in a case where the position and the posture of the subject 90 become the target position and the target posture. Consequently, the operator can easily recognize whether or not the position and the posture of the subject 90 become the target position and the target posture. As a result, the operator's convenience can be improved.

In the present embodiment, as described above, the notification unit 6e is configured to make display modes of the marker 40 different before and after the position and the posture of the subject 90 become the target position and the target posture. Consequently, the operator can easily visually recognize whether or not the position and the posture of the subject 90 become the target position and the target posture by checking the marker 40.

In the present embodiment, as described above, the projection unit 3 is provided in the vicinity of the X-ray irradiation unit 4, and is directed in the direction along the optical axis direction of the X-rays radiated from the X-ray irradiation unit 4. It is configured to project the marker 40. Consequently, when the subject 90 is imaged, the projection unit 3 is disposed in the vicinity of the X-ray irradiation unit 4 disposed at a position facing the subject 90, and thus the projection unit 3 can project the marker 40 from a position facing the subject 90. As a result, unlike a configuration in which the projection unit 3 is provided outside the vicinity of the X-ray irradiation unit 4 and projects the marker 40 from a direction intersecting an optical axis direction of X-rays, the projection unit 3 can radiate the marker 40 without adjusting a shape of the marker 40 according to an angle at the time of projecting the marker 40.

MODIFICATION EXAMPLES

It should be noted that the embodiment disclosed this time is exemplary in all respects and is not considered to be restrictive. The scope of the present invention is shown not by the description of the above embodiment but by the scope of claims, and further includes all changes (modification examples) within the meaning and the scope equivalent to the scope of claims.

For example, in the above embodiment, an example of the configuration in which the projection unit 3 projects the target contour line 40a onto the imaging position 80 has been described, but the present invention is not limited to this. For example, the projection unit 3 may be configured to project the subject target image 31 onto the imaging position 80.

Figure 16:
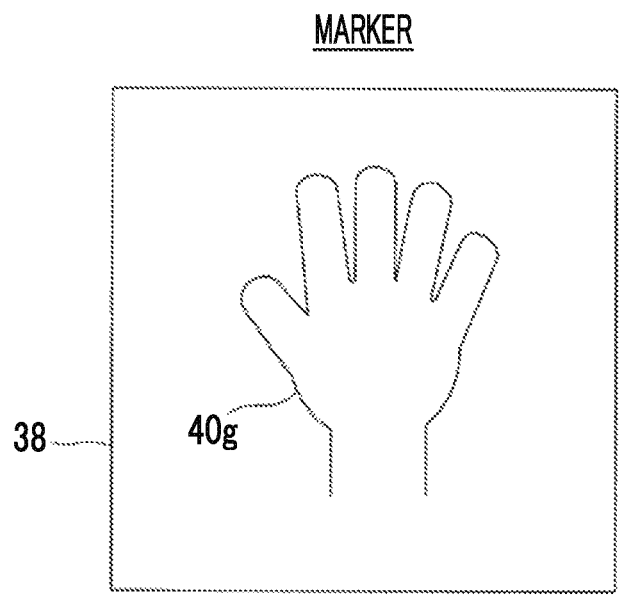
FIG. 16 is a schematic diagram for describing a target contour line acquired by the marker acquisition unit according to a modification example and projected by the projection unit.

In the above embodiment, an example of the configuration in which the X-ray imaging apparatus 1 is used for imaging the chest of the subject 90 has been described, but the present invention is not limited to this. For example, the X-ray imaging apparatus 1 may be used for imaging the hand or foot of the subject 90. In a case where the X-ray imaging apparatus 1 is used for imaging the hand of the subject 90, as in an image 38 illustrated in FIG. 16, the projection unit 3 may project a contour line 40g of the hand of the subject 90 as the marker 40. With this configuration, the subject 90 aligns a position of his/her hand with the projected contour line 40g of the hand, and can thus easily adjust a relative position of the hand with respect to the X-ray irradiation unit 4 and the X-ray detection unit 5. As a result, the subject 90 can align the relative position of the hand with respect to the X-ray irradiation unit 4 and the X-ray detection unit 5 by himself/herself without the operator (a doctor, a radiologist, or the like) performing the position adjustment, and thus it is possible to reduce a burden on the operator.

In the above embodiment, an example in which the X-ray imaging apparatus 1 is configured as a rounds imaging apparatus has been described, but the present invention is not limited to this. For example, the X-ray imaging apparatus may be configured as a so-called general imaging apparatus provided in an X-ray examination room or the like.

In the above embodiment, an example of the configuration in which the position information acquisition unit 6a acquires the target position and the target posture on the basis of the position and the posture of the subject 90 has been described, but the present invention is not limited to this. For example, the position information acquisition unit 6a may be configured to acquire only the target position on the basis of the position of the subject 90 without using the posture of the subject 90.

In the above embodiment, an example of the configuration in which the marker acquisition unit 6c acquires the target contour line 40a on the basis of the contour line 90b of the subject 90 and the center line 90d corresponding to the target position and the target posture has been described, but the present invention is not limited to this. For example, the marker acquisition unit 6c may be configured to acquire the target contour line 40a on the basis of the subject image 30 and the center line 90d. In this case, the second learned model 23a is generated by learning a learning model with an image in which the subject 90 is captured and the center line 90d of the subject 90 as training input data and the contour line 90b of the subject 90 as training output data.

In the above embodiment, an example of the configuration in which the marker acquisition unit 6c acquires the target contour line 40a on the basis of the contour line 90b of the subject 90 and the center line 90d corresponding to the target position and the target posture has been described, but the present invention is not limited to this. For example, the marker acquisition unit 6c may be configured to acquire the target contour line 40a on the basis of the imaging conditions 20 and the subject image 30. In this case, the second learned model 23a is generated by learning a learning model with the imaging conditions 20 and an image in which the subject 90 is captured as training input data and the contour line 90b of the subject 90 as training output data.

In the above embodiment, an example of the configuration in which the marker acquisition unit 6c acquires the target contour line 40a having the actual size of the subject 90 has been described, but the present invention is not limited to this. For example, the marker acquisition unit 6c may be configured to acquire a target contour line having a size other than the actual size of the subject 90. However, in a case of the configuration in which the marker acquisition unit 6c acquires a target contour line having a size other than the actual size of the subject 90, the size of the target contour line projected onto the imaging position 80 is different from the actual size of the contour line 90b of the subject 90. Thus, it becomes difficult for the operator to project a target contour line appropriate as a guide when adjusting the position of the subject 90. Therefore, it is preferable that the marker acquisition unit 6c is configured to acquire the target contour line 40a having the actual size of the subject 90.

In the above embodiment, an example of the configuration in which the center line acquisition unit 61 acquires the center line 90c of the subject 90 on the basis of the first learned model 22 has been described, but the present invention is limited to this. For example, the center line acquisition unit 61 may be configured to acquire the center line 90c of the subject 90 through image processing. As long as the center line 90c of the subject 90 can be acquired from the subject image 30, any configuration in which the center line acquisition unit 61 acquires the center line 90c may be employed.

In the above embodiment, an example of the configuration in which the marker acquisition unit 6c acquires the marker 40b indicating the movement direction of the subject 90 has been described, but the present invention is not limited to this. For example, the marker acquisition unit 6c does not have to acquire the marker 40b indicating the movement direction of the subject 90. The marker acquisition unit 6c may be configured to acquire the marker 40b indicating the movement direction of the X-ray detection unit 5. In this case, the target position acquisition unit 6b may acquire the current position of the X-ray detection unit 5, acquire the target position of the X-ray detection unit 5, and acquire the movement direction of the X-ray detection unit 5. Regarding the configuration in which the target position acquisition unit 6b acquires the current position of the X-ray detection unit 5, an existing technique such as acquiring position information of the X-ray detection unit 5 from the subject image 30 captured by the imaging unit 2 may be used.

In the above embodiment, an example of the configuration in which the marker acquisition unit 6c acquires the target position 41 of the X-ray detection region in the X-ray detection unit 5 has been described, but the present invention is not limited to this. For example, the marker acquisition unit 6c does not have to acquire the target position 41 of the X-ray detection region. However, in a case of the configuration in which the marker acquisition unit 6c does not acquire the target position 41 of the X-ray detection region, the rectangular marker 40c indicating the target position 41 of the X-ray detection region is not projected. Thus, it becomes difficult for the operator to recognize a position of the X-ray detection unit 5 appropriate for the imaging conditions 20. Therefore, it is preferable that the marker acquisition unit 6c is configured to acquire the target position 41 of the X-ray detection region.

In the above embodiment, an example in which the projection distance acquisition unit 8 is configured by an infrared scanner has been described, but the present invention is not limited to this. For example, the projection distance acquisition unit 8 may be configured to acquire the projection distance from an image captured by a stereo camera. The projection distance acquisition unit 8 may include a laser light source and a light detection unit, and may be configured to detect laser light radiated from the laser light source and reflected by a detection target (for example, the subject 90) to acquire a distance to the detection target. That is, the projection distance acquisition unit 8 may be configured as so-called light detection and ranging (LIDAR).

In the above embodiment, an example of the configuration in which the X-ray imaging apparatus 1 includes the marker shape adjustment unit 6d has been described, but the present invention is not limited to this. For example, the X-ray imaging apparatus 1 does not have to include the marker shape adjustment unit 6d. However, in a case where the X-ray imaging apparatus 1 does not include the marker shape adjustment unit 6d, the shape of the marker 40 is not adjusted according to an uneven shape of the surface of the imaging position 80. Thus, the visibility of the marker 40 may be reduced due to distortion of the shape of the marker 40 projected onto the imaging position 80. Therefore, it is preferable that the X-ray imaging apparatus 1 includes the marker shape adjustment unit 6d.

In the above embodiment, an example of the configuration in which the X-ray imaging apparatus 1 includes the notification unit 6e has been described, but the present invention is not limited to this. For example, the X-ray imaging apparatus 1 does not have to include the notification unit 6e. However, in a case where the X-ray imaging apparatus 1 does not include the notification unit 6e, it becomes difficult for the operator to easily understand that the position and the posture of the subject 90 become the target position and the target posture. Therefore, it is preferable that the X-ray imaging apparatus 1 includes the notification unit 6e.

In the above embodiment, an example of the configuration in which the notification unit 6e notifies that the position and the posture of the subject 90 become the target position and the target posture by making display modes of the marker 40 (target contour line 40a) different has been described, but the present invention is not limited to this. For example, the notification unit 6e may be configured to notify that the position and the posture of the subject 90 become the target position and the target posture with sound (notification sound), light (notification light), or the like. As long as the operator can understand that the position and the posture of the subject 90 become the target position and the target posture, any method of the notification unit 6e performing a notification may be used.

In the above embodiment, an example of the configuration in which the notification unit 6e notifies that the position and the posture of the subject 90 become the target position and the target posture has been described, but the present invention is not limited to this. For example, the notification unit 6e may be configured to notify that the position of the X-ray detection unit 5 becomes the target position 41. In this case, the notification unit 6e may notify that the position of the X-ray detection unit 5 becomes the target position 41 by making display modes of the contour line of the rectangular marker 40c projected on the target position 41 different, or filling the inside of the rectangular marker 40c with different colors.

In the above embodiment, an example of the configuration in which the projection unit 3 is provided in the vicinity of the X-ray irradiation unit 4 has been described, but the present invention is not limited to this. In a case where the X-ray imaging apparatus 1 is a rounds imaging apparatus, the projection unit 3 may be provided at any position as long as the projection unit 3 is provided at the X-ray imaging apparatus 1. In a case where the X-ray imaging apparatus 1 is a general imaging apparatus, the projection unit 3 may be provided at any position as long as the projection unit 3 is provided in an X-ray examination room.

In the above embodiment, an example of the configuration in which the X-ray imaging system 100 includes the X-ray imaging apparatus 1 provided with the imaging unit 2 and the projection unit 3 has been described, but the present invention is not limited to this. For example, the X-ray imaging system 100 may be configured with the X-ray imaging apparatus 1 and the imaging unit 2 and the projection unit 3 that are individually provided at positions different from that of the X-ray imaging apparatus 1.

In the above embodiment, an example of the configuration in which the marker acquisition unit 6c acquires the target contour line 40a or the subject target image 31 on the basis of selection or setting of the operator has been described, but the present invention is not limited to this. For example, the marker acquisition unit 6c may be configured to acquire both the target contour line 40a and the subject target image 31. The marker acquisition unit 6c may be configured to acquire only the target contour line 40a. In this case, the storage unit 7 may store only the second learned model 23a. The marker acquisition unit 6c may be configured to acquire only the subject target image 31. In this case, the storage unit 7 may store only the second learned model 23b.

In the above embodiment, as a process of projecting the marker 40, an example of a configuration in which the marker 40 as a moving image is projected in real time has been described, but the present invention is not limited to this. For example, the control unit 6 may be configured to acquire the marker 40 as a still image, and the projection unit 3 may be configured to project the marker 40 as a still image onto the imaging position 80. In this case, the control unit 6 may be configured to, when the position of the subject 90 captured in the subject image 30 is changed, acquire the marker 40 on the basis of the changed position of the subject 90.

Aspects

It will be understood by those skilled in the art that the above exemplary embodiments are specific examples of the following aspects.

Item 1

An X-ray imaging system including:
an X-ray irradiation unit that irradiates a subject with X-rays;
an X-ray detection unit that detects the X-rays radiated from the X-ray irradiation unit;
an imaging unit that acquires a subject image obtained by imaging an appearance of the subject;
a position information acquisition unit that acquires a position information of the subject captured in the subject image on the basis of the subject image;
a target position acquisition unit that acquires a target position according to imaging conditions on the basis of the imaging conditions and the position information; and
a projection unit that projects a marker indicating a contour of the subject for guiding a position of the subject to be the target position acquired by the target position acquisition unit, onto an imaging position that is the subject or a surface to which the subject is fixed.

Item 2

The X-ray imaging system according to item 1, in which
the target position acquisition unit is configured to acquire a target posture according to the imaging conditions along with the target position on the basis of the imaging conditions, the position information, and information regarding a posture of the subject, and
the projection unit is configured to project the contour of the subject for guiding the position and the posture of the subject to be the target position and the target posture as the marker onto the imaging position.

Item 3

The X-ray imaging system according to item 2, further including:
a marker acquisition unit that acquires the marker, in which
the marker acquisition unit is configured to acquire a target contour line that is a contour line when the subject takes the target posture at the target position, as the marker, and
the projection unit is configured to project at least the target contour line as the marker.

Item 4

The X-ray imaging system according to item 3, in which
the marker acquisition unit is configured to acquire the target contour line having an actual size of the subject as the marker, and
the projection unit is configured to project the target contour line having the actual size of the subject onto the imaging position.

Item 5

The X-ray imaging system according to item 3 or 4, in which
the position information acquisition unit includes
a contour line acquisition unit that acquires a contour line of the subject on the basis of the subject image, and
a center line acquisition unit that acquires a center line of the subject captured in the subject image,
the X-ray imaging system further includes a storage unit that stores reference information that is information regarding a reference position and a reference posture according to the imaging conditions,
the reference information includes a reference center line that is a center line of the subject when the subject takes the reference position and the reference posture, and
the target position acquisition unit is configured to acquire the target position and the target posture on the basis of the center line acquired by the center line acquisition unit and the reference center line.

Item 6

The X-ray imaging system according to item 5, in which
the center line acquisition unit is configured to acquire the center line on the basis of a first learned model in which acquisition of the center line of the subject from an image in which the subject is captured has been learned and the subject image.

Item 7

The X-ray imaging system according to item 5 or 6, in which
the marker acquisition unit is configured to acquire, as the marker, the target contour line when the subject takes the target posture at the target position, or a subject target image that is an image obtained by converting the subject captured in the subject image such that the subject has the target position and the target posture, on the basis of the subject image, the target position, and the target posture, and
the projection unit is configured to project the target contour line or the subject target image as the marker onto the imaging position.

Item 8

The X-ray imaging system according to item 7, in which
the marker acquisition unit is configured to acquire the target contour line or the subject target image on the basis of a second learned model in which acquisition of the target contour line of the subject from the center line of the subject has been learned or outputting of an image when the subject takes the target posture at the target position has been learned by using an image in which the subject is captured and the reference information, the reference information, the target position, and the target posture.

Item 9

The X-ray imaging system according to any one of items 3 to 8, in which
the target position acquisition unit is configured to acquire a movement direction for moving the subject to the target position on the basis of the position of the subject captured in the subject image and the target position,
the marker acquisition unit is configured to acquire the marker indicating the movement direction, and
the projection unit is configured to project the marker indicating the movement direction.

Item 10

The X-ray imaging system according to any one of items 3 to 9, in which
the marker acquisition unit is configured to acquire a target position of an X-ray detection region in the X-ray detection unit, and
The projection unit is configured to project the target position of the X-ray detection region onto the imaging position.

Item 11

The X-ray imaging system according to any one of items 3 to 9, in which the marker acquisition unit is configured to acquire at least one of a target distance between the X-ray irradiation unit and the X-ray detection unit, a target angle of the X-ray irradiation unit, and a target angle of the X-ray detection unit, and the projection unit is configured to project at least one of the target distance between the X-ray irradiation unit and the X-ray detection unit, the target angle of the X-ray irradiation unit, and the target angle of the X-ray detection unit onto the imaging position.

Item 12

The X-ray imaging system according to any one of items 2 to 11, further including:

a projection distance acquisition unit that acquires a projection distance that is a distance between the projection unit and the subject or a distance between the projection unit and a surface to which the subject is fixed; and a marker shape adjustment unit that adjusts a shape of the marker on the basis of the projection distance acquired by the projection distance acquisition unit, in which the projection unit is configured to project the marker of which the shape has been adjusted on the basis of the projection distance onto the imaging position.

Item 13

The X-ray imaging system according to any one of items 2 to 12, further including:

a notification unit that performs a notification in a case where the position and the posture of the subject become the target position and the target posture.

Item 14

The X-ray imaging system according to item 13, in which the notification unit is configured to make display modes of the marker different before and after the position and the posture of the subject become the target position and the target posture.

Item 15

The X-ray imaging system according to any one of items 1 to 14, in which the projection unit is provided in the vicinity of the X-ray irradiation unit, and is configured to project the marker in a direction along an optical axis direction of the X-rays radiated from the X-ray irradiation unit.

Item 16

An X-ray imaging apparatus including:

an X-ray irradiation unit that irradiates a subject with X-rays;

an X-ray detection unit that detects the X-rays radiated from the X-ray irradiation unit;

an imaging unit that acquires a subject image obtained by imaging an appearance of the subject;

a position information acquisition unit that acquires a position information of the subject captured in the subject image on the basis of the subject image;

a target position acquisition unit that acquires a target position according to imaging conditions on the basis of the imaging conditions and the position information; and a projection unit that projects a marker indicating a contour of the subject for guiding a position of the subject to be the target position acquired by the target position acquisition unit, onto an imaging position that is the subject or a surface to which the subject is fixed.

What is claimed is:

1. An X-ray imaging system comprising:

an X-ray irradiation unit that irradiates a subject with X-rays;

an X-ray detection unit that detects the X-rays radiated from the X-ray irradiation unit;

an imaging unit that acquires a subject image obtained by imaging an appearance of the subject;

a position information acquisition unit that acquires a position information of the subject captured in the subject image on the basis of the subject image;

a target position acquisition unit that acquires a target position according to imaging conditions on the basis of the imaging conditions and the position information; and a projection unit that projects a marker indicating a contour of the subject for guiding a position of the subject to be the target position acquired by the target position acquisition unit, onto an imaging position that is the subject or a surface to which the subject is fixed.

2. The X-ray imaging system according to claim 1, wherein the target position acquisition unit is configured to acquire a target posture according to the imaging conditions along with the target position on the basis of the imaging conditions, the position information, and information regarding a posture of the subject, and the projection unit is configured to project the contour of the subject for guiding the position and the posture of the subject to be the target position and the target posture as the marker onto the imaging position.

3. The X-ray imaging system according to claim 2, further comprising:

a marker acquisition unit that acquires the marker, wherein the marker acquisition unit is configured to acquire a target contour line that is a contour line when the subject takes the target posture at the target position, as the marker, and the projection unit is configured to project at least the target contour line as the marker.

4. The X-ray imaging system according to claim 3, wherein the marker acquisition unit is configured to acquire the target contour line having an actual size of the subject as the marker, and the projection unit is configured to project the target contour line having the actual size of the subject onto the imaging position.

5. The X-ray imaging system according to claim 3, wherein the position information acquisition unit includes a contour line acquisition unit that acquires a contour line of the subject on the basis of the subject image, and a center line acquisition unit that acquires a center line of the subject captured in the subject image, the X-ray imaging system further comprises a storage unit that stores reference information that is information regarding a reference position and a reference posture according to the imaging conditions, the reference information includes a reference center line that is a center line of the subject when the subject takes the reference position and the reference posture, and the target position acquisition unit is configured to acquire the target position and the target posture on the basis of the center line acquired by the center line acquisition unit and the reference center line.

6. The X-ray imaging system according to claim 5, wherein the center line acquisition unit is configured to acquire the center line on the basis of a first learned model in which acquisition of the center line of the subject from an image in which the subject is captured has been learned and the subject image.

7. The X-ray imaging system according to claim 5, wherein
the marker acquisition unit is configured to acquire, as the marker, the target contour line when the subject takes the target posture at the target position, or a subject target image that is an image obtained by converting the subject captured in the subject image such that the subject has the target position and the target posture, on the basis of the subject image, the target position, and the target posture, and
the projection unit is configured to project the target contour line or the subject target image as the marker onto the imaging position.

8. The X-ray imaging system according to claim 7, wherein
the marker acquisition unit is configured to acquire the target contour line or the subject target image on the basis of a second learned model in which acquisition of the target contour line of the subject from the center line of the subject has been learned or outputting of an image when the subject takes the target posture at the target position has been learned by using an image in which the subject is captured and the reference information, the reference information, the target position, and the target posture.

9. The X-ray imaging system according to claim 3, wherein
the target position acquisition unit is configured to acquire a movement direction for moving the subject to the target position on the basis of the position of the subject captured in the subject image and the target position,
the marker acquisition unit is configured to acquire the marker indicating the movement direction, and
the projection unit is configured to project the marker indicating the movement direction.

10. The X-ray imaging system according to claim 3, wherein
the marker acquisition unit is configured to acquire a target position of an X-ray detection region in the X-ray detection unit, and
the projection unit is configured to project the target position of the X-ray detection region onto the imaging position.

11. The X-ray imaging system according to claim 3, wherein
the marker acquisition unit is configured to acquire at least one of a target distance between the X-ray irradiation unit and the X-ray detection unit, a target angle of the X-ray irradiation unit, and a target angle of the X-ray detection unit, and the projection unit is configured to project at least one of the target distance between the X-ray irradiation unit and the X-ray detection unit, the target angle of the X-ray irradiation unit, and the target angle of the X-ray detection unit onto the imaging position.

12. The X-ray imaging system according to claim 2, further comprising:
a projection distance acquisition unit that acquires a projection distance that is a distance between the projection unit and the subject or a distance between the projection unit and a surface to which the subject is fixed; and
a marker shape adjustment unit that adjusts a shape of the marker on the basis of the projection distance acquired by the projection distance acquisition unit, wherein
the projection unit is configured to project the marker of which the shape has been adjusted on the basis of the projection distance onto the imaging position.

13. The X-ray imaging system according to claim 2, further comprising:
a notification unit that performs a notification in a case where the position and the posture of the subject become the target position and the target posture.

14. The X-ray imaging system according to claim 13, wherein
the notification unit is configured to make display modes of the marker different before and after the position and the posture of the subject become the target position and the target posture.

15. The X-ray imaging system according to claim 1, wherein
the projection unit is provided in the vicinity of the X-ray irradiation unit, and is configured to project the marker in a direction along an optical axis direction of the X-rays radiated from the X-ray irradiation unit.

16. An X-ray imaging apparatus comprising:
an X-ray irradiation unit that irradiates a subject with X-rays;
an X-ray detection unit that detects the X-rays radiated from the X-ray irradiation unit;
an imaging unit that acquires a subject image obtained by imaging an appearance of the subject;
a position information acquisition unit that acquires a position information of the subject captured in the subject image on the basis of the subject image;
a target position acquisition unit that acquires a target position according to imaging conditions on the basis of the imaging conditions and the position information; and
a projection unit that projects a marker indicating a contour of the subject for guiding a position of the subject to be the target position acquired by the target position acquisition unit, onto an imaging position that is the subject or a surface to which the subject is fixed.

* * * * *